US011331338B2

(12) United States Patent
Prinz et al.

(10) Patent No.: US 11,331,338 B2
(45) Date of Patent: May 17, 2022

(54) HYDROGEN SULFIDE RELEASING POLYMER COMPOUNDS

(71) Applicant: CROMA-PHARMA GESELLSCHAFT M.B.H., Leobendorf (AT)

(72) Inventors: Martin Prinz, Leobendorf (AT); Martin Hoffer, Vienna (AT)

(73) Assignee: CROMA-PHARMA GESELLSCHAFT M.B.H., Leobendorf (AT)

( * ) Notice: Subject to any disclaimer, the term of this patent is extended or adjusted under 35 U.S.C. 154(b) by 0 days.

(21) Appl. No.: 16/348,012

(22) PCT Filed: Nov. 7, 2017

(86) PCT No.: PCT/EP2017/078421
§ 371 (c)(1),
(2) Date: May 7, 2019

(87) PCT Pub. No.: WO2018/083326
PCT Pub. Date: May 11, 2018

(65) Prior Publication Data
US 2019/0298756 A1  Oct. 3, 2019

(30) Foreign Application Priority Data
Nov. 7, 2016 (EP) ..................... 16197625

(51) Int. Cl.
| C08B 37/08 | (2006.01) |
| C08B 37/00 | (2006.01) |
| C08B 15/00 | (2006.01) |
| A61K 31/728 | (2006.01) |
| A61P 17/10 | (2006.01) |
| A61P 17/02 | (2006.01) |
| A61K 8/73 | (2006.01) |
| A61K 9/00 | (2006.01) |
| A61K 9/06 | (2006.01) |
| A61K 31/726 | (2006.01) |
| A61Q 19/08 | (2006.01) |
| A61K 31/105 | (2006.01) |
| A61P 27/02 | (2006.01) |
| A61Q 19/00 | (2006.01) |
| A61P 17/18 | (2006.01) |
| A61P 17/00 | (2006.01) |
| A61K 31/795 | (2006.01) |
| A61P 19/02 | (2006.01) |

(52) U.S. Cl.
CPC ............ *A61K 31/728* (2013.01); *A61K 8/735* (2013.01); *A61K 8/736* (2013.01); *A61K 9/0019* (2013.01); *A61K 9/06* (2013.01); *A61K 31/105* (2013.01); *A61K 31/726* (2013.01); *A61K 31/795* (2013.01); *A61P 17/00* (2018.01); *A61P 17/02* (2018.01); *A61P 17/10* (2018.01); *A61P 17/18* (2018.01); *A61P 19/02* (2018.01); *A61P 27/02* (2018.01); *A61Q 19/00* (2013.01); *A61Q 19/08* (2013.01); *C08B 15/00* (2013.01); *C08B 37/003* (2013.01); *C08B 37/0045* (2013.01); *C08B 37/0069* (2013.01); *C08B 37/0072* (2013.01); *C08B 37/0084* (2013.01); *A61K 2800/91* (2013.01)

(58) Field of Classification Search
CPC ...... A61K 31/728; A61K 8/735; A61K 8/736; A61K 31/105; A61K 31/795; C08B 37/0072; C08B 37/003; C08B 37/0045; C08B 37/0084; C08B 37/0069; C08B 15/00
See application file for complete search history.

(56) References Cited

U.S. PATENT DOCUMENTS

| 6,451,337 | B1 * | 9/2002 | Smith | .......... A61K 47/61 424/400 |
| 8,182,830 | B2 * | 5/2012 | Chen | .......... A61L 27/14 424/423 |
| 9,096,504 | B2 | 8/2015 | Xian et al. | |
| 2007/0197479 | A1 | 8/2007 | Wallace | |
| 2010/0028399 | A1 | 2/2010 | Hornof | |
| 2010/0198338 | A1 | 8/2010 | Chen | |
| 2011/0165216 | A1 | 7/2011 | Chen | |
| 2013/0253051 | A1 | 9/2013 | Xian | |

FOREIGN PATENT DOCUMENTS

| WO | WO97/04012 | 2/1997 |
| WO | WO2006/119258 | 11/2006 |
| WO | WO 2008/077172 | 7/2008 |
| WO | WO2009/003624 | 1/2009 |
| WO | WO2009/109501 | 11/2009 |
| WO | WO2010/065784 | 6/2010 |
| WO | WO2011/084204 | 7/2011 |
| WO | WO2011/124380 | 10/2011 |
| WO | WO2015/169728 | 11/2015 |
| WO | WO2016/161445 | 10/2016 |
| WO | 2 482 852 | 11/2017 |

OTHER PUBLICATIONS

Law, C.-H. et al., Toxicology, "Hyaluronic acid-dependent protection in H9C2 cardiomyocytes: A cell model of heart ischemia-reperfusion injury and treatment", 2013, vol. 303, pp. 54-71 (Year: 2013).*

Hongyok Teeravee, et al., "Effect of chitosan-N-acetylcysteine conjugate in a mouse model of botulinum toxin B-induced dry eye", Suppression and Regression of Choroidal Neovascularization by the Multitargeted Kinase Inhibitor Pazopanib, vol. 127, No. 4, Apr. 1, 2009.

(Continued)

*Primary Examiner* — Bahar Craigo
(74) *Attorney, Agent, or Firm* — Workman Nydegger

(57) ABSTRACT

The invention provides a hydrogen sulfide releasing polymer compound having a polysaccharide backbone, wherein the compound has at least two substructures, and wherein said substructures are capable of releasing hydrogen sulfide by thiol activation as well as uses thereof. Additionally, a method of treatment and prevention of a skin condition, an ocular disease or osteoarthritis is provided.

12 Claims, 11 Drawing Sheets

(56) References Cited

OTHER PUBLICATIONS

Salvatore Palumbo, et al., "In situforming hydrogels of new amino hyaluronic acid/benzoyl-cysteine derivatives as potential scaffolds for cartilage regeneration", Soft Matter, vol. 8, No. 18, Jan. 1, 2012, p. 4918.
Zhao, et al., "Controllable Hydrogen Sulfide Donors and Their Activity against Myocardial Ischemia-Reperfusion Injury", ACS Chemical Biology, vol. 8, No. 6, Jun. 21, 2013, pp. 1283-1290.
Roger, et al., "New Biologically Active Hydrogen Sulfide Donors", Chembiochem—A European Journal of Chemical Biology., vol. 14, No. 17, Nov. 25, 2013, pp. 2268-2271.
Zhao, Y.; Biggs, T.D.; Xiang, M. "Hydrogen sulfide (H2S) releasing agents: chemistry and biological applications". Chem Commun, 2014; 50:11788.
Williams Frances MK, et al., "Dietary garlic and hip osteoarthritis: evidence of a protective effect and putative mechanism of action", BMC Musculoskeletal Disorders, Biomed Central, London, GB, vol. 11, No. 1, Dec. 8, 2010, p. 280.
Wang, G.; Li, W.; Chen, Q.; Jiang, Y.; Lu, X.; Zhao, X. "Hydrogen sulfide accelerates wound healing in diabetic rats." Int J Clin Exp Pathol. May 2015; 8:5097-104.
Yang et al. "A Novel Controllable Hydrogen Sulfide-Releasing Molecule Protects Human Skin Keratinocytes Against Methylglyoxal-Induced Injury and Dysfunction." Cell Physiol Biochem 2014, Author manuscript; available in PMC Sep. 2015; 34:1304-1317.
Feng, S.; Zhao, Y; Xian, M.; Wang Q. "Biological thiols-triggered hydrogen sulfide releasing microfibres fortissue engineering applications." Acta Biomaterialia Nov. 2015; 27:205-213.
Biermann, Lagreze et al., May 2011, Inhalative preconditioning with hydrogen sulfide attenuated apoptosis after retinal ischemia/reperfusion injury, Mol Vis (17): 1275-1286).
Li, Fox et al., 2013, The complex effects of the slow-releasing hydrogen sulfide donor GYY4137 in a model of acute joint inflammation and in human cartilage cells, J Cell Mol Med (17): Dec. 4, 2012; 365-376.
Sieghart, et al., 2015, Hydrogen sulphide decreases IL-1 beta-induced activation of fibroblast-like synoviocytes from patients with osteoarthritis, J Cell Mol Med (19): Jul. 2014187-197.
Foster, J. C.; Matson J. B.; Functionalization of Methacrylate Polymers with Thioximes: A Robust Postpolmerization Modification Reaction and a Method for the Preparation of H2S-Releasing Polymers, Macromolecules, Jul. 2014, 47, 5089-5095.
Carter, J.M.; Qian, Y.; Foster, J.C.; Matson, J.B.; Peptide-based hydrogen sulfide-releasing gels; Chem. Commun., Jul. 2015, 51, 13131.
Hasegawa, U.; van der Vlies, A.L.; Design and Synthesis of Polymeric hydrogen sulfide donors; Bioconjugate Chemistry, Jun. 2014, 25, 1290-1300).
Boateng, Matthews et al., Aug. 2008, Wound healing dressings and drug delivery systems: a review, J Pharm Sci (97): 2892-2923.
Dai, et al., Jul. 2011, Chitosan preparations for wounds and burns: antimicrobial and wound-healing effects, Expert Rev Anti Infect Ther (9): 857-879.
Schramm, Spitzer et al., Feb. 2012, The cross-linked biopolymer hyaluronic acid as an artificial vitreous substitute, Invest Ophthalmol Vis Sci (53): 613-621.
Brockmeier, Sep. 2006, Viscosupplementation therapy for osteoarthritis, Sports Med Arthrosc (14): 155-162.

Oprenyeszk, Chausson et al., Apr. 2013, The intra-articular injection of a new chitosan biomaterial prevents the progression of osteoarthritis in ACLT rabbit model, Osteoarthritis and Cartilage (21): S69.
Hombach, et al., Jan. 2008, Thiolated chitosans: development and in vitro evaluation of an oral tobramycin sulphate delivery system, Eur J Pharm Sci (33): 1-8.
Schmitz, Grabovac et al., Jun. 2007 Synthesis and characterization of a chitosan-N-acetyl cysteine conjugate, Int J Pharm 2008 (347): 79-85.
Clausen, et al., The Role of Glutathione in the Permeation Enhancing Effect of Thiolated Polymers, Pharmaceutical Research, vol. 19, No. 5, May 2002.
Hornof ,et al., May 2008, Evaluation of Thiolated Polymers With Antioxidative Properties for the Use in Artificial Tears, Investigative Ophthalmology & Visual Science (49): 113-113.
Hugh-Bloch, et al., May 2008, Disulfide Crosslinked Hyaluronic Acid Films for Ocular Drug Delivery, Investigative Ophthalmology & Visual Science (49): 5773-5773.
Shindo, Witt et al., Jan. 1994, Enzymic and non-enzymic antioxidants in epidermis and dermis of human skin, J Invest Dermatol (102): 122-124.
Rose, Richer et al., Apr. 1998, Ocular oxidants and antioxidant protection, Proc Soc Exp Biol Med (217): 397-407.
Rhie, Shin et al., May 2001, Aging- and photoaging-dependent changes of enzymatic and nonenzymic antioxidants in the epidermis and dermis of human skin in vivo, J Invest Dermatol (117): 1212-1217.
Angthong, Morales et al., Dec. 2013, Can levels of antioxidants in synovial fluid predict the severity of primary knee osteoarthritis: a preliminary study, Springerplus (2): 652.
Honnegowda, Kumar et al., Jan.-Apr. 2015, Effects of limited access dressing in chronic wounds: A biochemical and histological study, Indian J Plast Surg (48): 22-28).
Burguera, et al., Effect of hydrogen sulfide sources on inflammation and catabolic makers on interleukin 1-stimulated human articular chondrocytes, Apr. 2014, Osteoathritis and Cartilage 22 (2014) 1026-1035.
Clausen, et al., Thiolated Biopolymers: New Polymers for Ocular Use, ARVO Annual Meeting Abstract, May 2008.
Tyler R. Long et al: "Long-term release of a thiobenzamide from a backbone functionalized poly(lactic acid)" Polymer Chemistry. Oct. 2015; vol. 6, No. 40, pp. 7188-7195.
Francesca Ercole et al: "Macromolecular Hydrogen Sulfide Donors Trigger Spatiotemporally Confined Changes in Cell Signaling" Biomacromolecules, Dec. 2015, vol. 17, pp. 371-383.
Written Opinion dated Feb. 23, 2018, issued in PCT/EP2017/078421, filed Nov. 7, 2017.
International Search Report dated Feb. 23, 2018, issued in PCT/EP2017/078421, filed Nov. 7, 2017.
Martelli, Alma, et al., "Arylthioamides as H2S Donors: L-Cysteine-Activated Releasing Properties and Vascular Effects in Vitro and in Vivo", ACS Medical Chemistry Letters, 2013, 4, 904-908, Aug. 8, 2013.
Chen Huijun et al. 2015: "Hydrogen Sulfide amelioed the healing of mouse skin injury", Cheng Huijun et al., Journal of Henan University (Medical Science), vol. 34, No. 1, Mar. 2015, pp. 32-35.
Han Yuyi et al. 2016: "Progress in potential treatment of hydrogen sulfide for ophthalmic diseases", Han Yuyi et al., New Progress in Ophthalmology, Apr. 2016, vol. 36, No. 4, pp. 390-395.
Wan Maoxian "Overview of Research on Biological Function of Hydrogen Sulfide", Journal of Hanshan Normal University, vol. 34, No. 6, pp. 77-86.

* cited by examiner

HYDROGEN SULFIDE RELEASING POLYMER COMPOUNDS

The invention relates to hydrogen sulfide releasing polymer compounds and uses thereof.

BACKGROUND

Hydrogen sulfide ($H_2S$) is a biological signalling molecule. Its function seems to be comparable and potentially linked with the better investigated gaseous transmitter nitric oxide (NO). Hydrogen sulfide is believed to be involved in processes like angiogenesis and inflammation. $H_2S$ and/or $H_2S$ releasing compounds were shown to have an anti-inflammatory effect, inhibit apoptosis in vascular endothelial cells and cardiomyocytes, and induce vasodilatation. Being a gaseous compound, hydrogen sulfide is difficult to administer. Thus, various concepts of hydrogen sulfide releasing compounds were established. An overview is given by Zhao et al (Zhao, Y.; Biggs, T. D.; Xiang, M. Hydrogen sulfide ($H_2S$) releasing agents: chemistry and biological applications. Chem Commun, 2014; 50:11788).

The hydrogen sulfide releasing compounds include for example
- compounds releasing $H_2S$ by hydrolysis such as inorganic sulfide salts ($Na_2S$ and NaHS), Lawesson's reagent derivative GYY4137, phosphorodithioates and 1,2-dithiol-3-thiones (DTTs) such as 5-(4-hydroxyphenyl)-3H-1,2-dithiole-3-thione (ADT-OH),
- compounds releasing $H_2S$ upon light activation (geminal dithiol compounds, ketoprofenate-caged compounds),
- and compounds releasing $H_2S$ by thiol activation.

A major disadvantage of all compounds which release hydrogen sulfide by hydrolysis is their instability in aqueous solution. Once these compounds are dissolved in water hydrogen sulfide is released in an uncontrollable manner.

WO 2016/161445 describes $H_2S$ donors, which release hydrogen sulfide upon contact with unmasking agents through cyclization of the precursor compound via lactone or lactam formation. The examples rely on an enzymatic mechanism with an esterase as biological unmasking agent. The precursor compounds may include a moiety being a drug or a sugar.

Also cysteine and N-acetylcysteine can be a $H_2S$ source under specific circumstances in vivo. N-acetylcysteine may be transformed to cysteine and certain pyridoxyl 5'-phosphate depending enzymes may produce $H_2S$ from cysteine (US 2007/0197479).

Of special interest are $H_2S$ releasing compounds with a thiol activation mechanism. They release $H_2S$ in the presence of a reaction partner containing a free thiol group. The reaction partner may be naturally present at the site of administration (biological and endogenous), or may be an externally administered reaction partner (exogenous). The thiol activation mechanism allows controlled or environment-dependent release of said gas from these hydrogen sulfide releasing compounds. The group of substructures, which release $H_2S$ with a thiol activation mechanism, include for example
- perthiols, wherein the —SSH group is protected, resulting in an (—SSR) substructure (see also U.S. Pat. No. 9,096,504)
- N-(acylthio)-benzamides, also called N-mercapto-based $H_2S$ donors (such as the N-(benzoylthio)benzamide NSHD1 resp. $H_2S$ Donor 5a),
- dithioperoxyanhydrides,
- arylthioamides, and
- garlic-derived sulphur compounds, like diallyl-disulfide and -trisulfide.

One potential application area for $H_2S$ releasing compounds are skin-related disorders, especially diabetic wounds. Wang et al. showed improved wound healing in diabetic rats using a 2% sodium bisulfide ointment (Wang, G.; Li, W.; Chen, Q.; Jiang, Y.; Lu, X; Zhao, X. Hydrogen sulfide accelerates wound healing in diabetic rats. Int J Clin Exp Pathol. 2015; 8:5097-104). Yang et al. described that the N-mercapto-based $H_2S$ donor NSHD1 has beneficial effects in a keratinocyte model of diabetic wounds (Yang et al. A Novel Controllable Hydrogen Sulfide-Releasing Molecule Protects Human Skin Keratinocytes Against Methylglyoxal-Induced Injury and Dysfunction. Cell Physiol Biochem 2014; 34:1304-1317). A potential application in the field of tissue engineering was proposed by Feng et al., studying fibres of the synthetic polymer polycaprolactone (PCL) as a carrier for admixed $H_2S$ Donor NSHD1 using electrospinning (Feng, S.; Zhao, Y; Xian, M.; Wang Q. Biological thiols-triggered hydrogen sulfide releasing microfibres for tissue engineering applications. Acta Biomaterialia 2015; 27:205-213).

Another potential application area for $H_2S$ releasing compounds is the prevention and treatment of ocular diseases such as glaucoma, inflammatory conditions such as conjunctivitis (WO 2006/119258, WO 2009/109501), and retinal diseases such as macular degeneration, retinal vascular occlusion and diabetic retinopathy (Biermann, Lagreze et al., 2011, Inhalative preconditioning with hydrogen sulfide attenuated apoptosis after retinal ischemia/reperfusion injury, Mol Vis (17): 1275-1286).

Another potential application area for $H_2S$ releasing compounds is the prevention and treatment of osteoarthritis. This widespread disease is characterized by persistent inflammation and joint destruction. Recent studies have found $H_2S$ to be a mediator in inflammatory joint diseases, where it exhibited anti-inflammatory, anti-catabolic and/or antioxidant effects in in vitro models using human synoviocytes and articular chondrocytes (Li, Fox et al., 2013, The complex effects of the slow-releasing hydrogen sulfide donor GYY4137 in a model of acute joint inflammation and in human cartilage cells, J Cell Mol Med (17): 365-376; Burguera, Vela-Anero et al., 2014, Effect of hydrogen sulfide sources on inflammation and catabolic markers on interleukin 1beta-stimulated human articular chondrocytes, Osteoarthritis Cartilage (22): 1026-1035). Positive results were also obtained when $H_2S$ was administered as a sulphurous water bath or via dietary uptake of garlic (Williams, Skinner et al., 2010, Dietary garlic and hip osteoarthritis: evidence of a protective effect and putative mechanism of action, BMC Musculoskelet Disord (11): 280; Sieghart, Liszt et al., 2015, Hydrogen sulphide decreases IL-1beta-induced activation of fibroblast-like synoviocytes from patients with osteoarthritis, J Cell Mol Med (19): 187-197). These findings suggest that exogenous supplementation of $H_2S$ may provide a viable therapeutic option for these diseases.

A methacrylate-based polymer with a pendant S-aroylthiooxime (SATO) substructure was described by Foster and Matson (Foster, J. C.; Matson J. B.; Functionalization of Methacrylate Polymers with Thioximes: A Robust Postpolmerization Modification Reaction and a Method for the Preparation of $H_2$S-Releasing Polymers, Macromolecules, 2014, 47, 5089-5095). Polymers with different molecular weights ranging from 8500 Da to 40500 Da were prepared. The same group also developed peptide-based hydrogen sulfide-releasing gels with a terminal SATO functionality, wherein the peptide has a molecular weight of ~1 kDa and thus, is not a polymer (Carter, J. M.; Qian, Y.; Foster, J. C.;

Matson, J. B.; Peptide-based hydrogen sulfide-releasing gels; Chem. Commun., 2015, 51, 13131). A polyethylene conjugate with the DTT substructure 5-(4-hydroxy-phenyl)-3H-1,2-dithiole-3-thione was described by Hasegawa and van der Vlies (Hasegawa, U.; van der Vlies, A. L.; Design and Synthesis of Polymeric hydrogen sulfide donors; Bioconjugate Chemistry, 2014, 25, 1290-1300). The polyethylene glycol used as polymeric backbone for the conjugate had a nominal molecular weight of 5000 Da. The conjugate showed reduced cytotoxicity compared to ADT-OH but enhanced the production of the pro-inflammatory cytokine tumor necrosis factor (TNF-$\alpha$) in a cellular assay. WO 2011/084204 discloses a hydrogen sulfide releasing polymer, wherein the hydrogen sulfide releasing substructure is a thioamide readily hydrolysable in presence of water and the polymer backbone is a synthetic polymer such as a methacrylate derivative. The molecular weight of a thioamide modified polymer according to the invention was 77696 Da. It was suggested to use the $H_2S$ releasing polymer for coating of medical devices, i.e. implants such as stents. Also US 2010/198338 describes $H_2S$ releasing polymers for coating or forming medical devices. The compounds have at least one basic group bound to $H_2S$ and in the examples a methacrylate copolymer with tertiary amine in the side chain is complexed with gaseous $H_2S$.

SHORT DESCRIPTION OF THE INVENTION

It is an object of the present invention to provide a polymer compound which releases hydrogen sulfide in a controlled manner and is suitable for local application in treatment or prevention of skin conditions (including skin disease or cosmetic condition), ocular diseases and osteoarthritis.

The invention provides a hydrogen sulfide releasing polymer compound, wherein the polymer has a polysaccharide backbone and wherein the compound has at least two substructures and wherein said substructures are capable of releasing hydrogen sulfide by thiol activation. Moreover, the invention provides the compound for use as a medicament and use of the compound as a cosmetic.

The inventors synthesised polysaccharide derivatives with covalently bound substructures, which were shown to release $H_2S$ in a controlled manner upon contact with an activating thiol group containing agent (s. examples). These hydrogen sulfide releasing polymer compounds are valuable for above mentioned applications, e.g. skin conditions, and combine the beneficial effects of the polysaccharide polymer (e.g. forming a hydrogel with swelling capacity; lubrication) with the beneficial effects of liberated $H_2S$. Preferably, the hydrogen sulfide releasing polymer compound with a polysaccharide backbone will absorb water or wound fluid and will not spontaneously dissolve or disperse therein. A gel formed by the hydrogen sulfide releasing polymer compound with a polysaccharide backbone according to the invention is also suitable as a dermal filler, intraocular implant or vitreous substitute. A film formed by the hydrogen sulfide releasing polymer compound with a polysaccharide backbone according to the invention is suitable to separate tissues and prevent adhesion of tissues post-surgery. An aqueous solution comprising a hydrogen sulfide releasing polymer compound with a polysaccharide backbone according to the invention is suitable as lubricating eye drop. Moreover, a gel with a hydrogen sulfide releasing polymer compound with a polysaccharide backbone according to the invention is suitable as viscosupplement for prevention and treatment of osteoarthritis. Such a viscosupplement allows to exploit the therapeutic effects of $H_2S$ and to improve the lubricating properties of the synovial fluid. The polymer compounds according to the invention liberate hydrogen sulfide in a controlled manner by reaction i.e. in the presence of a biological (endogenous) or externally administered reaction partner containing a free thiol (—SH) group. Hydrogen sulfide is set free only in presence of the reaction partner, which allows controlled or environment-dependent release of said gas. In absence of a reaction partner, the polymer compounds are stable in the sense that they do not release hydrogen sulfide and may be formulated for example as stable aqueous solution. Thus, the polymer compounds overcome the disadvantage of compounds releasing hydrogen sulfide by hydrolysis.

Thus, the present invention especially provides a hydrogen sulfide releasing polymer compound that may be used as an implantable, biodegradable and biocompatible filler, intraocular implant, vitreous substitute or viscosupplement, i.e. for subcutaneous, intradermal, intraocular and intraarticular injection, or as a dressing for topical dermal applications promoting wound healing (e.g. diabetic ulcers or burn wounds) and/or ameliorate scarring, or as eye drop for ocular applications. None of the hydrogen sulfide releasing polymers according to the prior art includes a polysaccharide polymer backbone, at least two hydrogen sulfide releasing substructures and was suggested for the use in treatment or prevention of skin conditions, ocular diseases or osteoarthritis.

Thus, the invention provides a polymeric $H_2S$ releasing compound for use in treatment and prevention of skin disease, for use in treatment and prevention of ocular diseases and for use in treatment and prevention of osteoarthritis as well as cosmetic uses or methods of uses of these compounds.

DETAILED DESCRIPTION OF THE INVENTION

The following definitions of terms and preferred embodiments relate equally to the compound according to the invention and the compound for use or the use of the compound according to the invention as well as methods of using the compound according to the invention, where applicable.

A hydrogen sulfide releasing compound according to the invention should be understood as a compound that is capable of liberating hydrogen sulfide gas under appropriate conditions. The term release may be understood synonymously to liberating or setting free, i.e. the hydrogen sulfide releasing compound may also be classified as hydrogen sulfide donor.

The polymer compound according to the present invention further comprises at least two substructures, wherein said substructures are capable of releasing hydrogen sulfide by thiol activation. This functional feature defines substructures that release hydrogen sulfide by a thiol activation mechanism. Different classes of such substructures have been described in literature. The suitable substructures are organic and include at least one covalently bound sulphur atom. They share the common concept that upon contact with a thiol group (—SH) bearing reaction partner, the release of hydrogen sulfide is activated/triggered. Accordingly, presence of substructures capable of releasing hydrogen sulfide by thiol activation in a polymer compound can easily be verified by contacting the compound with a reaction partner comprising a thiol group under conditions that allow the detection of gaseous hydrogen sulfide. As used in the following, the terms "substructure" or "hydrogen sulfide releasing substructure" refers to a substructure being capable of releasing hydrogen sulfide by thiol activation if not indicated otherwise.

Preferably, the invention refers to compounds that are capable of releasing hydrogen sulfide in presence of a thiol group containing reaction partner under conditions physiologically occurring in or at the surface of human skin, in or at the surface of human eyes or in human joints, e.g. at temperatures between 20 to 40° C. and at pH values of 4 to 8, preferably at pH values of 4 to 7.

Preferably, the substructures capable of releasing hydrogen sulfide by thiol activation are selected from the group consisting of acyl-protected perthiols, N-(acylthio)-benzamides, dithioperoxyanhydrides, arylthioamides, and garlic-derived sulphur compounds.

Moreover, it should be noted that a hydrogen sulfide releasing polymer compound refers to a polymer compound which itself is able to release $H_2S$ and is not a mixture of a polymeric compound and a $H_2S$ releasing compound. The at least two substructures capable of releasing hydrogen sulfide by thiol activation are part of the polymer structure. With the hydrogen sulfide releasing polymer compound, the starting material is provided as a functional unit and the release kinetics will not be influenced by mixing and decomposition properties of potential carrier material(s) and an admixed $H_2S$ donor.

In a polymer compound according to the invention or in a polymer compound for use according to the invention, the backbone is a polysaccharide. Polysaccharides provide the feature of excellent biocompatibility. Examples for suitable polysaccharides may be selected from the group consisting of hyaluronic acid (sodium hyaluronate, hyaluronan, HA), cellulose derivatives, such as carboxymethyl cellulose, sodium or calcium salt of alginic acid, chondroitin sulfate, dermatan sulfate, chitosan and chitosan derivatives, such as trimethyl chitosan and other quaternized chitosan derivatives and carboxyl modified chitosan derivatives, such as carboxymethyl chitosan, and pectin. These polysaccharides have functional groups that allow for a derivatisation. Especially, suitable polysaccharide polymers have a functional group selected from amine or carboxyl group. The inventors exemplarily proved that modified hyaluronic acid with a $H_2S$ releasing substructure showed good tolerability with different cell lines. In a compound (for use) according to the invention, wherein the backbone is a polysaccharide, preferably, the polysaccharide is selected from the group consisting of chitosan and hyaluronic acid (HA). Chitosan and hyaluronic acid both are well characterized as biocompatible materials being able to form hydrogels, which is an advantageous aspect of the present invention in the context of dermal applications (Boateng, Matthews et al., 2008, Wound healing dressings and drug delivery systems: a review, J Pharm Sci (97): 2892-2923; Dai, Tanaka et al., 2011, Chitosan preparations for wounds and burns: antimicrobial and wound-healing effects, Expert Rev Anti Infect Ther (9): 857-879), intradermal applications (WO 97/04012, WO 2010/065784, WO 2011/124380), local ocular applications (WO 2015/169728), intraocular applications (Schramm, Spitzer et al., 2012, The cross-linked biopolymer hyaluronic acid as an artificial vitreous substitute, Invest Ophthalmol Vis Sci (53): 613-621) and viscosupplementation (Brockmeier and Shaffer, 2006, Viscosupplementation therapy for osteoarthritis, Sports Med Arthrosc (14): 155-162; Oprenyeszk, Chausson et al., 2013, The intra-articular injection of a new chitosan biomaterial prevents the progression of osteoarthritis in ACLT rabbit model, Osteoarthritis and Cartilage (21): S69). Moreover, the polysaccharides, especially chitosan and hyaluronic acid, are capable of absorbing wound exudate (secreted wound fluid). Also thiol group containing chitosan and hyaluronic acid derivatives have been described before (Hongyok, T., 2009, Effect of chitosan-N-acetylcysteine conjugate in a mouse model of botulinum toxin B-induced dry eye; Arch. Ophthalmol. 127:525-532; US2010/0028399 A1; Palumbo Salvatore, F., 2012; In situ forming hydrogels of new amino hyaluronic acid/ benzoyl-cysteine derivatives as potential scaffolds for cartilage regeneration), e.g. with N-acetylcysteine or benzoyl-cysteine in the side chains. Although comprising cysteine derivatives, these polymers are neither intended for nor capable of releasing hydrogen sulfide by thiol activation.

Suitable $H_2S$ releasing polymer compounds according to the invention with a chitosan backbone preferably have a mean molecular weight in the range of 20 kDa to 500 kDa, for example a molecular weight of approximately 150 kDa. Suitable polymer compounds according to the invention with a hyaluronic acid backbone preferably have a mean molecular weight in the range of 20 kDa to 3 MDa, preferably 90 kDa to 3 MDa for example approximately 600 kDa. Generally, the polymeric character of the compound according to the invention is reflected in a mean molecular weight preferably above 10 kDa, more preferably, above 25 kDa or above 50 kDa. For example the polymer may have a mean molecular weight between 10 kDa to 3 MDa, such as e.g. 50 kDa to 1000 kDa, or 100 kDa to 600 kDa or 100 kDa to 300 kDa.

The polymer compound according to the present invention further may be described by comprising a polysaccharide backbone of repetitive units of monosaccharides, disaccharides or oligosaccharides and at least two substructures being covalently attached to the polysaccharide backbone, for example via a linker. Thus, the hydrogen sulfide releasing substructures can be described as part of a side chain of the polymer compound. With at least two hydrogen sulfide releasing substructures, at least two of the repetitive units of the backbone of a polymer will show the respective modification introducing the hydrogen sulfide releasing substructures. Generally, the extent to which the polysaccharide backbone shows the modification may be expressed as degree of modification. Preferably, the degree of modification with hydrogen sulfide releasing substructures per g polymer is above 10 µM substructures per g polymer, more preferably, above 50 µM or above 100 µM. For example, the polymer may have a degree of modification with hydrogen sulfide releasing substructures per g polymer between 10 µM to 1000 µM, such as e.g. 50 µM to 500 µM or 100 µM to 300 µM.

In a preferred embodiment, the polymer compound according to the invention comprises a substructure according to the formula I

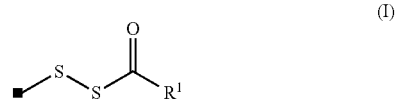

wherein $R^1$ is an alkyl, an alkenyl, an alkinyl, an alkylaryl, an aralkyl or an aryl, preferably selected out of the group consisting of phenyl or methyl, and wherein the square indicates the point, where the substructure is linked to the polysaccharide backbone of the hydrogen sulfide releasing polymer compound (also referred to as attachment point).

Preferred compounds according to this embodiments are polysaccharide-bound acyl-protected perthiols. According to the inventors knowledge polysaccharide-bound acyl-protected perthiols have not been described before. The inventors were able to show that these polymer compounds release hydrogen sulfide, triggered by the presence of a thiol compound such as the amino acid L-cysteine, cysteamine or the antioxidant glutathione. The polymeric character and the high viscosity of an aqueous preparation of the polymer compound did not inhibit the liberation of $H_2S$.

In formula I, preferably, $R^1$ is $C_1$ to $C_3$ alkyl, such as methyl, ethyl, prop-1-yl, or prop-2-yl, or aryl, such as phenyl. Consequently, the protection group of the perthiol is for example an acetyl or a benzoyl group. Preferably, $R^1$ is methyl, i.e. the protection group is acetyl. A perthiol derivative of hyaluronic acid with an acetyl protection group showed a higher level of $H_2S$ release than the benzoyl analogue.

Preferably, at least two acyl-protected perthiol substructures are linked to the polysaccharide backbone via a linker L. A preferred hydrogen sulfide releasing polymer compound according to the invention thus comprises at least two units according to formula II

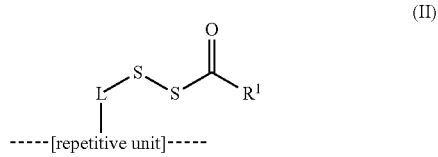

wherein $R^1$ is an alkyl, an alkenyl, an alkinyl, an alkylaryl, an aralkyl or an aryl, preferably selected out of the group consisting of phenyl or methyl, wherein the repetitive unit is part of the polysaccharide backbone, which polysaccharide backbone is indicated by the dashed line, and wherein L is a linker. The units according to formula II fall under formula I and the same preferences as in formula I apply for each $R^1$. The linker L forms a linkage between the substructure and a repetitive unit, preferably by forming a first bond to the substructure and a second bond to the repetitive unit, i.e. to an atom of a repetitive unit forming part of the polysaccharide backbone. Of course, the polymer compounds may preferably comprise further substructures according to formula I, wherein preferably any further substructures is included in a further unit according to formula II.

In general, various concepts can be applied for the linker L. The linker L can include various chemical groups depending on the nature of the polysaccharide backbone. For example, the linker may be connected with an amide bond, wherein either the carboxyl part or the amine part of the amide bond is part of the polysaccharide backbone, i.e. the repetitive unit. It is preferred that the polysaccharides forming the polymer backbone provide amine or carboxyl groups for attachment of functionalized linkers (s. preferred polysaccharides above). Hyaluronic acid for example comprises glucuronic acid units and N-acetylglucosamine units.

Preferably, the carboxyl group of a glucuronic acid unit is modified with an amine based linker. Chitosan comprises glucosamine units, wherein preferably the amine is modified with a carboxyl based linker. Exemplarily, FIG. 1 shows acyl-protected perthiol-modified chitosan and hyaluronic acid.

These examples are in accordance with a preferred embodiment, wherein the linker is selected out of the group consisting of formula III

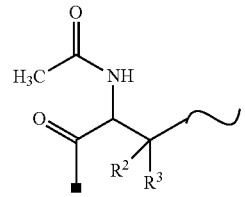

and formula IV

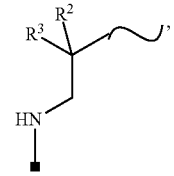

wherein the square indicates the attachment point to the polysaccharide backbone, i.e. a repetitive unit of the polysaccharide backbone of the hydrogen sulfide releasing polymer compound and the tilde the attachment point to the substructure according to formula I, and wherein $R^2$ and $R^3$ are independently selected out of the group consisting of hydrogen, alkyl or aryl.

In one embodiment, it might be preferred that $R^2$ and $R^3$ are not hydrogen, i.e. resulting in a tertiary perthiol. Tertiary perthiols were previously described in context of low molecular weight $H_2S$ donors (U.S. Pat. No. 9,096,504).

An acyl-protected perthiol-comprising polymer with a chitosan backbone and a linker of the formula III, wherein $R^2$ and $R^3$ are both hydrogen, relates to chitosan modified with N-acetyl cysteine (NAC). NAC-chitosan was previously described as a biocompatible polymer with various beneficial effects which are especially useful for drug delivery purposes and for ophthalmic applications (Hombach, Hoyer et al., 2008, Thiolated chitosans: development and in vitro evaluation of an oral tobramycin sulphate delivery system, Eur J Pharm Sci (33): 1-8; Schmitz, Grabovac et al., 2008, Synthesis and characterization of a chitosan-N-acetyl cysteine conjugate, Int J Pharm (347): 79-85; WO 2015/169728).

An acyl-protected perthiol-comprising polymer with a hyaluronic acid backbone and a linker of the formula IV, wherein $R^2$ and $R^3$ are both hydrogen, relates to hyaluronic acid modified with cysteamine which has been described before (Clausen, Homof et al., 2008, Thiolated Biopolymers: New Polymers for Ocular Use, Investigative Ophthalmology & Visual Science (49): 5770-5770; Homof, Hoffer et al., 2008, Evaluation of Thiolated Polymers With Antioxidative Properties for the Use in Artificial Tears, Investigative Ophthalmology & Visual Science (49): 113-113; Hugh-Bloch, Homof et al., 2008, Disulfide Crosslinked Hyaluronic Acid Films for Ocular Drug Delivery, Investigative Ophthalmology & Visual Science (49): 5773-5773); WO 2008/077172 "Use of polymers").

In other aspects, the invention provides the compound according to the invention for use as a medicament and the use of the compounds as a cosmetic. Also in these aspects, the hydrogen sulfide releasing polymer comprises a polysaccharide backbone and at least two substructures capable of releasing hydrogen sulfide by thiol activation and optionally shows other preferences as disclosed above.

Based on the findings of the present invention, the benefits of the compounds according to the invention extend over the related polymers without $H_2S$ releasing property and should be useful in treatment and prevention of skin conditions, ocular diseases and osteoarthritis.

The application areas for the compounds according to the invention include skin conditions of medical nature, i.e. skin diseases as well as cosmetic skin conditions. Thus, in one aspect the invention provides the use of a compound according to the invention as a cosmetic. It should be noted that the terms cosmetic or medicament as used herein may also refer to a medical device or a medical product. In one aspect, the invention provides the compound according to the invention for use or use of the compound according to the invention in treatment and prevention of a skin condition. The skin condition is a skin disease in case of compound for use or a cosmetic skin condition in case of use of a compound.

In one embodiment, the skin disease may be a skin injury, i.e. a wound, such as a torn, cut, puncture, lesion, aberration, burn or ulcer, especially an open wound. The influence on wound healing may be mediated by the anti-oxidative, inflammation-modulating and angiogenetic properties of $H_2S$. Especially, the treatment may be beneficial in those phases of wound healing wherein inflammation plays an important role as well as during maturation and remodelling. The wound may also be a chronic wound, such as a wound associated with diabetes, venous or arterial disease, infection, and metabolic deficiencies of old age. The skin disease may also be a scar, i.e. a skin mark indicating a previous wound.

In another embodiment, the skin disease may be of an acute or chronic inflammatory nature, such as sun burn, inflammatory reactions following exposure to allergens or contact with chemical irritants, psoriasis or dermatitis (eczema).

In another embodiment, the use relates to use as a cosmetic for a skin condition of cosmetic nature, i.e. a cosmetic skin condition, wherein the skin shows for example signs of age or other undesired, non-medical skin phenomena. Exemplarily, the cosmetic use includes use for treatment and prevention of skin wrinkles and fine lines, as well as the treatment of skin areas, which show other signs of ageing, such as decreased elasticity (elastosis), broken capillaries and sun damage.

In another aspect, the invention provides the compound according to the invention for use in treatment and prevention of an ocular disease, wherein the compound is a hydrogen sulfide releasing polymer. Exemplarily, the ocular disease may be selected from the group consisting of glaucoma, inflammatory conditions such as conjunctivitis, and retinal diseases such as macular degeneration, retinal vascular occlusion and diabetic retinopathy.

In another aspect, the invention provides the compound according to the invention for use in treatment and prevention of osteoarthritis, wherein the compound is a hydrogen sulfide releasing polymer. In one embodiment, it may be preferred that the osteoarthritis is a secondary arthritis associated with an inflammatory disease and/or a chronic arthritis (Lyme disease's arthritis, rheumatoid arthritis, psoriasis arthritis).

Using the compounds according to the invention for treatment and prevention of above described diseases and/or conditions will include that the compound or a composition comprising the compound is applied to a subject, e.g. a human being. Local application is preferred and is understood as application to a specific location, i.e. the application site, e.g. a skin area, ocular tissues (more generally the eye) or a joint of a subject to be treated, wherein at said site the skin condition, ocular disease or osteoarthritis occurs or is expected to occur, respectively.

In case of use for treating and preventing a skin condition (skin disease or cosmetic skin condition) a local application, preferably a dermal application, should be understood in that the application is performed at a defined part of the skin, e.g. to a skin area, wherein the skin condition occurs or is expected to occur. The local application may include treating a skin area superficially, intradermally or subcutaneously, i.e. by injection under the skin area of issue. In a preferred embodiment, the compound for use according to the invention is administered onto or into a skin area, wherein the skin area shows the (cosmetic or medical) skin condition or wherein the skin area is suspected to develop the skin condition.

In case of use for treating and preventing ocular diseases a local application to the ocular tissues (more generally to the eye) is preferred. The local application may include applying the compound for use according to the invention on the ocular surface, e.g. in the form of eye drops, or by injection into the eye. The compound for use according to the invention may be administered as vitreous body substitute or as intraocular implant. A vitreous body substitute is injected as a gel into the posterior of the eye after a vitrectomy. An intraocular implant is injected into the eye or implanted during ocular surgery. In embodiments, wherein the compound for use according to the invention is administered onto the ocular surface (in compositions being eye drops, eye gels, etc.), $H_2S$ released by the compound may also have an effect to other parts of the eye. Liberated $H_2S$ may diffuse to these other parts, and thus, the compound may have an effect on diseases related to non-superficial parts of the eye such as diseases involving the retina or glaucoma.

In case of use for treating and preventing osteoarthritis a local application to a joint is preferred, wherein said joint shows the osteoarthritis or wherein said joint is suspected to develop the osteoarthritis. The compound for use according to the invention may be administered as viscosupplement. A viscosupplement is injected as a gel into the joint of issue, e.g. knee, referred to as intraarticular injection. A compound or composition administered as viscosupplement is also referred to as implant.

A composition for applying the compound according to the invention includes the compound according to the invention and one or more suitable excipients. A composition including a compound according to the invention may be a medicament, a cosmetic or a medical device or medical product. A pharmaceutically acceptable excipient comprised in a composition according to the invention may be selected out of the group consisting of appropriate carrier and/or diluent, e.g. including fillers, binders, disintegrants, flow conditioners, lubricants, fragrances, preservatives, stabilizers, wetting agents and/or emulsifiers, solubilizers, salts for regulating osmotic pressure and/or buffers. The composition may also comprise polymeric excipients such as chitosan and/or hyaluronic acid. The composition may also comprise stabilized polymers such as crosslinked hyaluronic acid.

Some polymer compounds with a polysaccharide backbone, for example hyaluronic acid, pectin, sodium alginate, carboxymethyl cellulose or chitosan, may form hydrogels with water, thus the composition may be provided as a hydrogel. The gel may be applied topically onto the skin or onto the ocular surface. The composition may be an injectable implant for applying the compound intradermally or subcutaneously as dermal filler. The composition may be an injectable implant for applying the compound as vitreous body substitute or intraocular implant. The composition may also be an injectable implant for applying the compound as intra-articular viscosupplement.

A composition for applying the compound according to the invention may also include one or more other active substances, for example from the group of vitamins, antiphlogistic agents, antirheumatic agents, analgesics, anti-infective agents, antiviral agents, antibiotics, antimycotics, antiseptic agents, chemotherapeutic agents, cytostatic agents, local anesthetics, antiallergic agents, antihistamines, anti-inflammatory agents and growth factors.

In order to provide a compound according to the invention or a composition comprising a compound according to the invention, a person skilled in the art would envisage different application forms depending on the intended use. Application forms of the compound may be in the form of a wound dressing or dermal patch, e.g. as gel forming agent in hydrocolloid dressings in combination with other materials such as adhesives or as hydrogel dressing.

Such wound dressings may be gels, thin sheets, films or multi-layered composite dressings.

The compound may also be provided in the form of beads, flakes, powder and threads and prepared in the form of a film, a fibrous pad, a web, a woven or non-woven fabric, a freeze-dried sponge, a foam or combinations thereof. Other topical formulations for applying the compound include liquid (solutions, e.g. solutions for eye drops, suspensions and emulsions) and semi-solid preparations (gels, ointments and creams). In case of compositions intended for use in treatment at open wounds or treatment at the eye or compositions for use by injection, they should be provided as sterilised application form. In the examples 6 to 19 different application forms are presented.

As discussed previously, $H_2S$ releasing polymer compounds comprising substructures capable of releasing hydrogen sulfide by thiol activation react with free thiol groups (—SH) to release $H_2S$. Thus, a compound according to the invention is preferably applied/administered in combination with a thiol-group containing reaction partner that allows for a triggered release of $H_2S$ from preferred compounds. Alternatively, the $H_2S$ release may rely on reaction partners with free thiol groups, which occur naturally at the site of application.

In one embodiment, the compound for use according to the invention or the use of this compound includes that the compound is administered to a local application site (i.e. to a specific location at the body, e.g. a skin area, eye or a joint) and simultaneously or sequentially a thiol-group containing reaction partner is administered to the application site.

Simultaneous or sequential administration allows for a combined therapy of the hydrogen sulfide releasing polymer compound according to the invention and the thiol-group containing reaction partner. Combined application should provide the reaction partners in conditions that allow them to react with each other. Especially local proximity, i.e. direct contact, must be provided for the reaction which is for example the case when both are administered to the same skin area. A skin area may be a place or spot of skin wherein the size of the area may depend on the respective condition of the skin.

In this context, simultaneous or sequential should mean that the compound according to the invention and the thiol-group containing reaction partner are administered at around the same time. As preferred option according to the invention, "simultaneously" indicates a temporal coincidence. "Sequentially" may indicate that either the thiol-group containing reaction partner or the compound according to the invention is applied first. However, in the context of the invention preferably, "sequentially" should preferably indicate that the two compounds are applied directly one after the other.

While it is preferred that the compound according to the invention and the thiol-group containing reaction partner are co-administered, they should not be allowed to react with each other during preparation of the application form or storage. In one aspect of the invention, the compound according to the invention and the thiol-group containing reaction partner are not provided in the same composition. In order to provide a suitable application form for simultaneous application, the person skilled in the art will concept a suitable single dose kit or packaging, wherein the polymer according to the invention and the thiol-group containing reaction partner may be stored and provided separately, including an instruction how they are mixed shortly prior to or during administration.

The examples disclose application forms that allow for co-administration of the compound according to the invention and a thiol-group containing reaction partner. More generally, different forms may be described as follows: For example, upon opening the single dose kit or package, the $H_2S$ releasing polymer containing composition "A" and a composition of a thiol-group containing reaction partner "B" are mixed prior to or during administration to form the final topical composition: a user (e.g. patient, user of a cosmetic product, medical staff) opens a single dose package, the user empties the chambers of the package into his or her palm, or into a suitable mixing container, and then mixes the composition A, e.g. containing a $H_2S$ releasing hyaluronic acid derivative, with the composition B, e.g. containing L-cysteine, to form the final topical composition prior to applying the topical composition to the affected area. Alternatively, the user may apply the composition A first to the affected skin area, immediately followed by the application of the composition B to the same skin area. In an alternative embodiment, a single dose package with two separate chambers containing composition A and B, respectively is provided. The user opens a single dose package and empties the chambers of the package directly onto the affected area of skin. The composition A and composition B, e.g. containing a $H_2S$ releasing hyaluronic acid derivative and L-cysteine respectively, are then mixed as the user rubs the compositions into the affected area of skin. In a further preferred embodiment, the compound for use according to the invention is administered from a (multi dose) dual chambered apparatus containing separate chambers to hold the composition A and the composition B. In one example of such an apparatus, a dispenser is able to simultaneously dose the two compositions separately contained in the chambers by pressing a dosing head, which subsequently dispenses the two compositions in approximately equal volumes. A further embodiment for administering the topical compositions of the present subject matter is a two-compartment tube, with the composition A in one compartment and the composition B in the other compartment. The two compartments are separated by a thin membrane which is disrupted when the user attempts to empty the tube, which allows mixing of the two components prior to application.

In each of the alternative packaging embodiments, composition A and composition B are mixed just prior to or during administration to form the final topical composition. In case of application by injection, i.e. intradermal or subcutaneous injection for preventing and treating skin condition (including a skin disease and a cosmetic condition), intraocular injection for preventing and treating ocular diseases and intraarticular injection for preventing and treating osteoarthritis, a compound for use according to the invention is provided in an injectable composition. For example composition "A" comprising the compound is filled into single dose syringes and sterilized with moist heat. A thiol-group containing reaction partner can also be applied via injection, i.e. provided as sterile solution and this composition "B" may be injected to the same side i.e. at the same skin area, ocular application site or into the same joint. Dual chamber syringes also allow a simultaneous administration by injection of two compositions. However, especially in case of injection (e.g. examples 9, 10-15), the co-administration of a composition B might be omitted, as the thiol-group containing reaction partner for triggering the release of $H_2S$ may be provided within the skin, ocular tissues or in the synovial fluid (s. below).

In one embodiment the thiol-group containing reaction partner is an organic compound of low molecular weight, e.g. about 500 Da or below. Small organic compounds may access the hydrogen sulfide releasing substructures even in context of a polymer agglomerate such as a hydrogel or an implant formed by the polymer compound. Steric hindrance can be an issue for an enzyme based activation mechanism because the enzymes as high molecular weight compounds may be not easily access the hydrogen sulfide releasing substructures in a polymer arrangement. However, for compounds according to the invention capable of releasing hydrogen sulfide by thiol activation small activating agents (thiol-group containing reaction partners) are available. In a preferred embodiment the thiol-group containing reaction partner is selected out of the group consisting of cysteine, cysteamine, N-acylcysteine, homocysteine and glutathione. Glutathione should be understood as referring to reduced glutathione. Preferably, cysteine is L-cysteine, and N-acylcysteine is N-acetylcysteine.

In another embodiment, the thiol-group containing reaction partner may also be a thiolated polymer, for example thiolated chitosan, thiolated hyaluronic acid or other thiolated polysaccharides. For example, the composition comprises a $H_2S$ releasing compound with a polysaccharide backbone and a thiol-group containing reaction partner, wherein the thiol-group containing reaction partner is a thiolated polysaccharide with the same or a different polysaccharide backbone as the $H_2S$ releasing compound.

In another embodiment, the thiol-group containing reaction partner may be a substance naturally occurring in the skin, in the eye, in granulation tissue during wound healing, in wound exudate, or in synovial fluid, such as reduced glutathione (Shindo, Witt et al., 1994, Enzymic and nonenzymic antioxidants in epidermis and dermis of human skin, J Invest Dermatol (102): 122-124; Rose, Richer et al., 1998, Ocular oxidants and antioxidant protection, Proc Soc Exp Biol Med (217): 397-407; Rhie, Shin et al., 2001, Aging- and photoaging-dependent changes of enzymic and nonenzymic antioxidants in the epidermis and dermis of human skin in vivo, J Invest Dermatol (117): 1212-1217; Angthong, Morales et al., 2013, Can levels of antioxidants in synovial fluid predict the severity of primary knee osteoarthritis: a preliminary study, Springerplus (2): 652; Honnegowda, Kumar et al., 2015, Effects of limited access dressing in chronic wounds: A biochemical and histological study, Indian J Plast Surg (48): 22-28). Thus, especially in context of administering via injection or treating an open wound, it might not be necessary to co-administer an exogenous thiol-group containing reaction partner to trigger $H_2S$ release from the polymer.

In a further aspect the invention relates to method of treating or preventing a condition, wherein the condition is selected from the group consisting of a skin condition (including a skin disease or a cosmetic condition), an ocular disease or osteoarthritis, the method comprising the steps of
   i) providing a compound according to the present invention and
   ii) administering the compound to a local application site, wherein the condition occurs or is expected to occur at said site.

The local site may be a skin area, an ocular tissue or a joint, in case the method relates to treating or preventing a skin condition, an ocular disease or osteoarthritis, respectively.

Administering to a skin area is considered for treating or preventing skin condition and the local application might be topical but also subcutaneous or intradermal injection as discussed above. In case of treating and prevention of an ocular disease, the step of administering might include topical application to the ocular surface but also intraocular injection as described above. In case of treating and prevention of osteoarthritis local application as described in step ii) means that the compound should be administered to a joint, and preferably the compound is administered via intraarticular injection. In one embodiment, the method of treating or preventing includes a further step of simultaneously or sequentially administering a thiol-group containing reaction partner at the same local application site.

In a preferred embodiment, the method is a method of preventing and treating cosmetic skin conditions, thus, the method is a cosmetic method and not related to treating or preventing a disease but a skin condition of cosmetic nature.

The invention will now be described in more detail by figures and the non-limiting examples.

FIG. 1 shows exemplary schemes for hydrogen sulfide releasing polymer compounds according to the invention, wherein FIGS. 1A and 1B both show a hyaluronic acid with acyl-protected perthiol substructures and FIG. 1C shows a chitosan with acyl-protected perthiol substructures.

FIG. 2 schematically shows the synthesis scheme of the polymer of FIG. 1C.

FIG. 3 schematically shows the synthesis scheme of the polymer of FIG. 1A.

FIG. 4 schematically shows an alternative synthesis scheme of the polymer of FIG. 1A.

FIG. 5 schematically shows the synthesis scheme of the polymer of FIG. 1B.

Figure 8A:
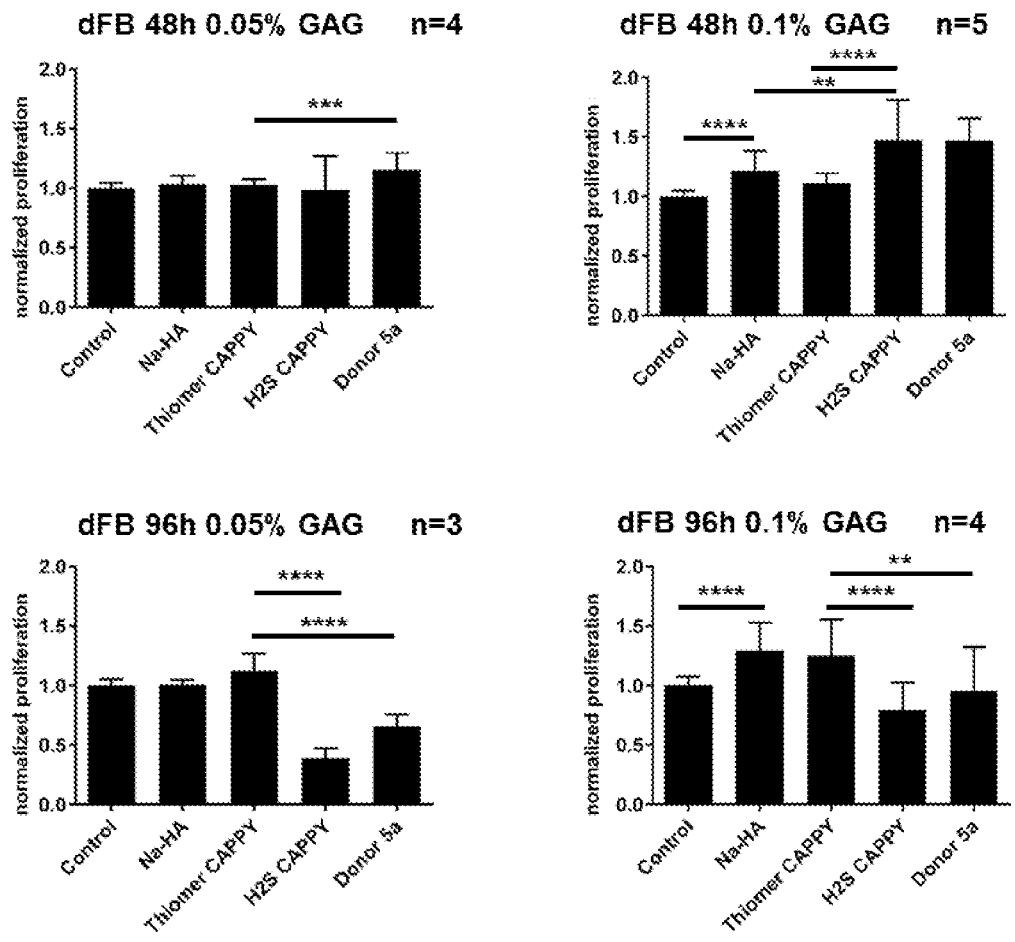
Figure 8B:
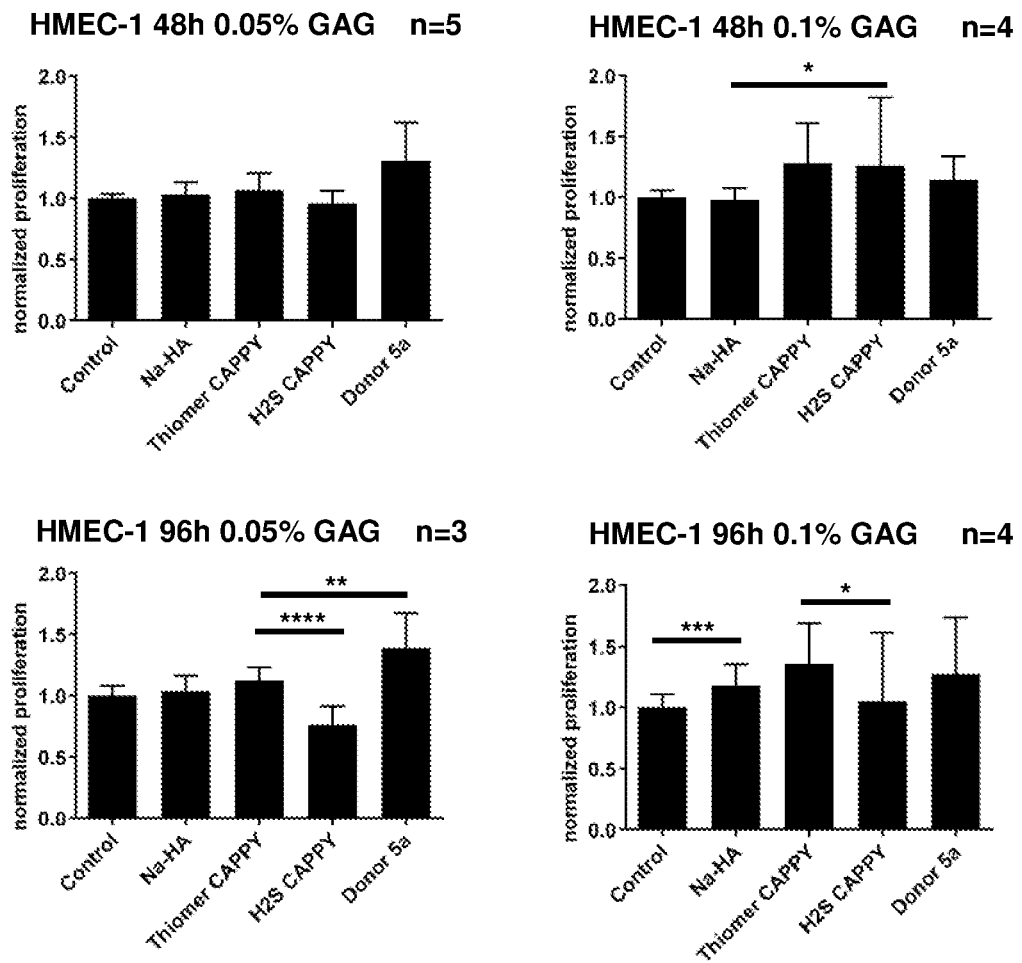
Figure 8C:
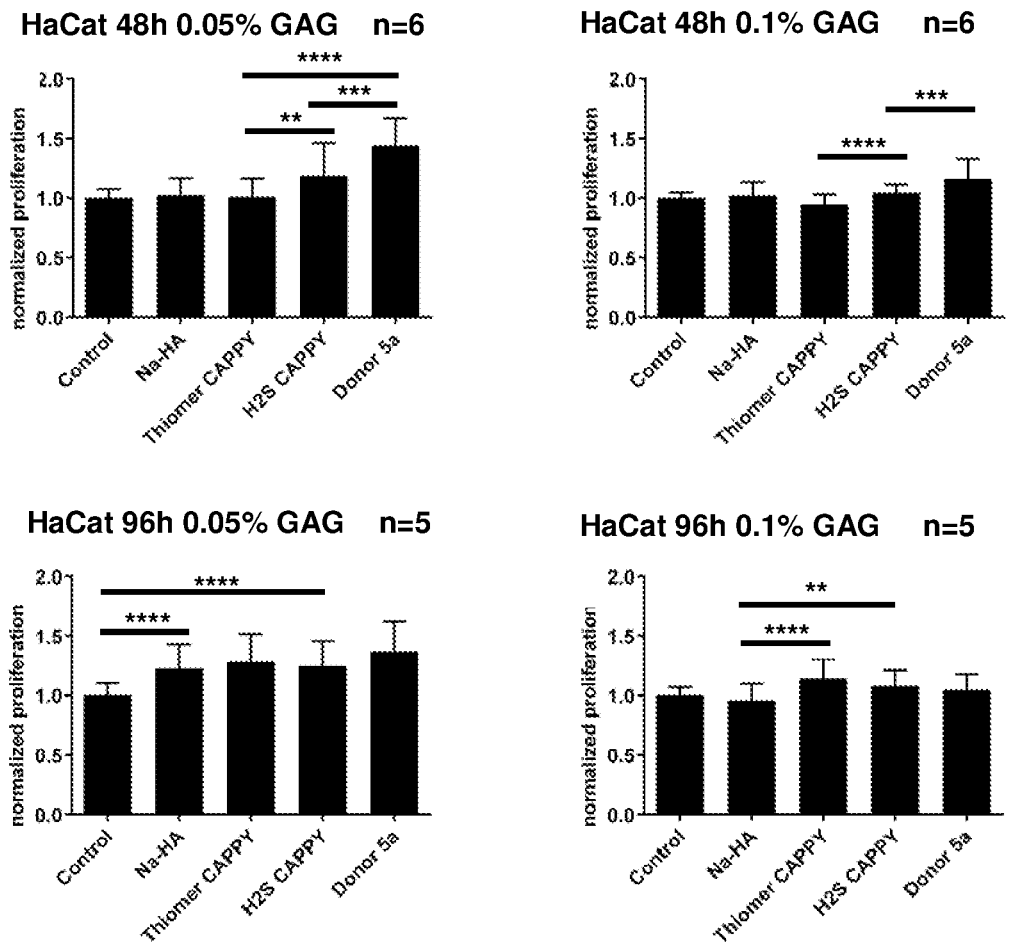

FIG. 8 shows results from cell compatibility assays, wherein the investigated cell lines were primary human dermal fibroblasts (dFb) (FIG. 8A), immortalized human microvascular endothelial cells (HMEC-1) (FIG. 8B), and keratinocytes from the cell line HaCat (FIG. 8C). "% GAG" indicates the investigated concentration of the investigated compounds. Significance is calculated using an unpaired Student's T-test, wherein results are indicated by stars according to * for p<0.05;  for p<0.01; *for p<0.005, and **** for p<0.001.

Figure 9:
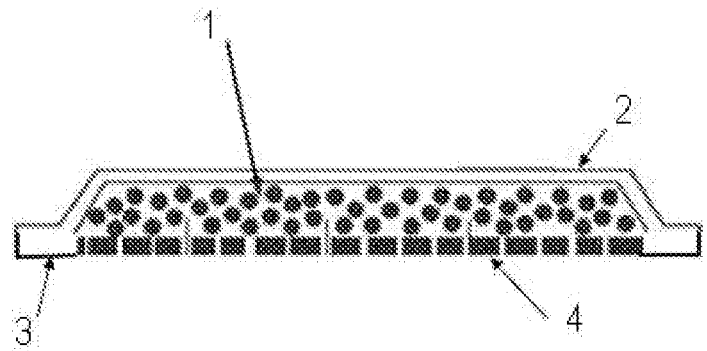

FIG. 9 schematically shows the structure of a multi-layer wound dressing.

Figure 10A:
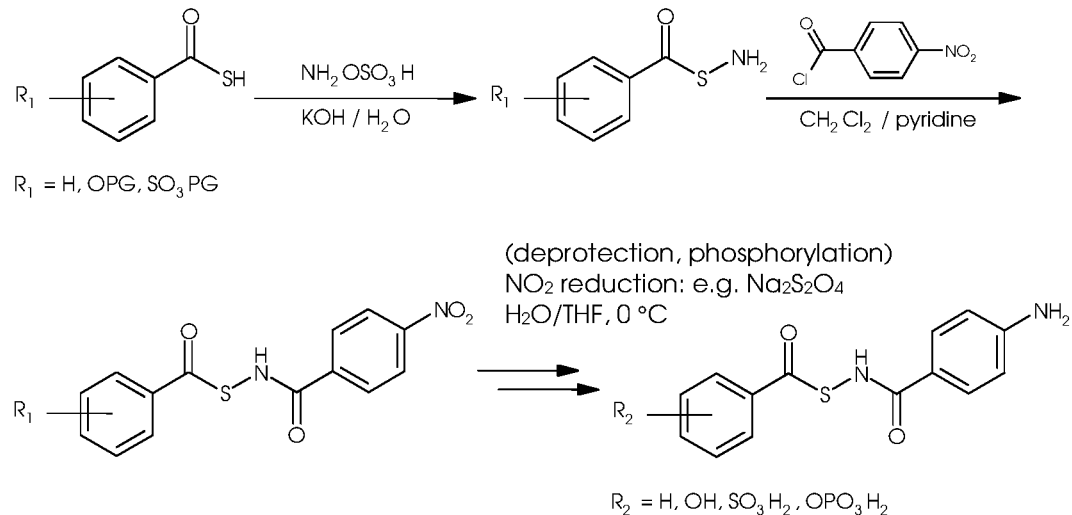
Figure 10B:
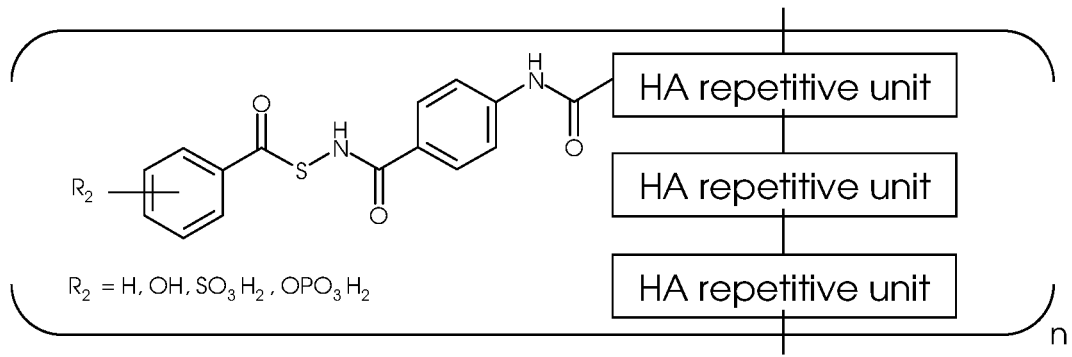

FIG. 10 shows the preparation of a N-(benzoylthio) benzamide derivative and a $H_2S$ releasing hyaluronic acid derivative with covalently attached N-(benzoylthio)benzamide substructures. FIG. 10A shows a reaction scheme for the synthesis of a derivative of $H_2S$ Donor 5a modified with an amino group. FIG. 10B shows a $H_2S$ releasing hyaluronic acid derivative with covalently attached N-(benzoylthio) benzamide substructures.

In the schemes, the polymer compounds are visualized by a section of the polymer and the brackets indicate that these sections are multiplied, i.e. multiplied n-times within the polymer. It will be appreciated that the schemes are of symbolic nature and the relation of unmodified and modified repetitive units does not represent an actual degree of modification.

EXAMPLES

Example 1: Generation of a $H_2S$-Releasing Chitosan Derivative

Figure 1A:
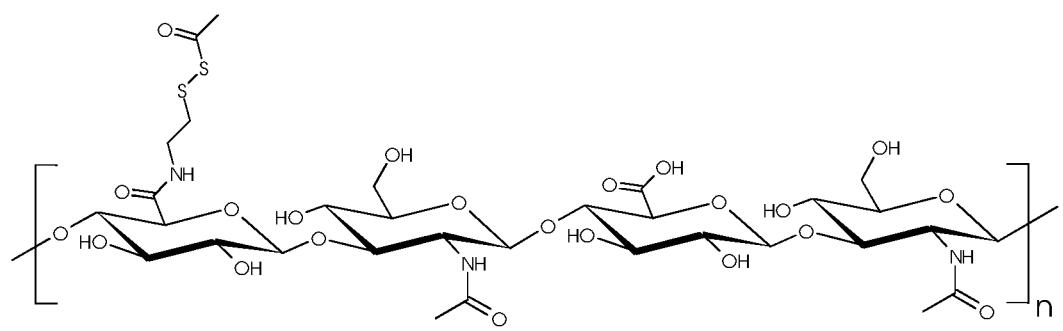
Figure 1B:
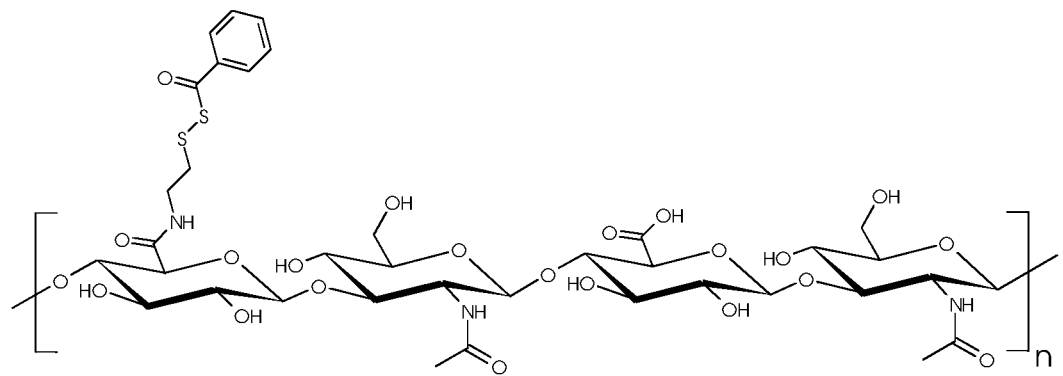
Figure 1C:
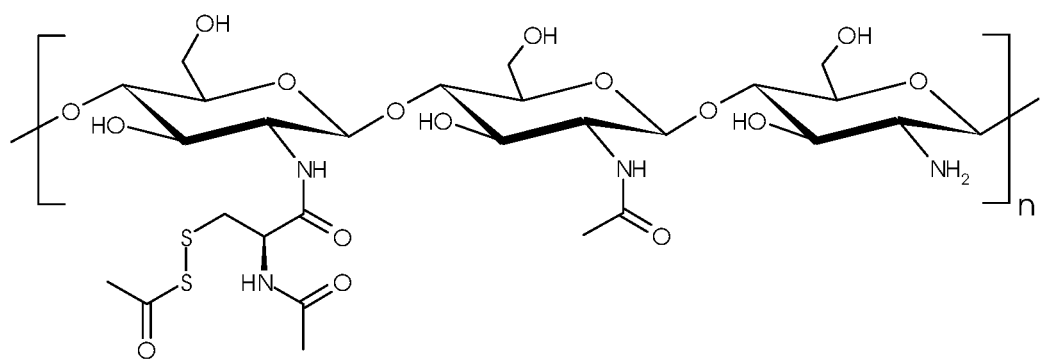
Figure 2:
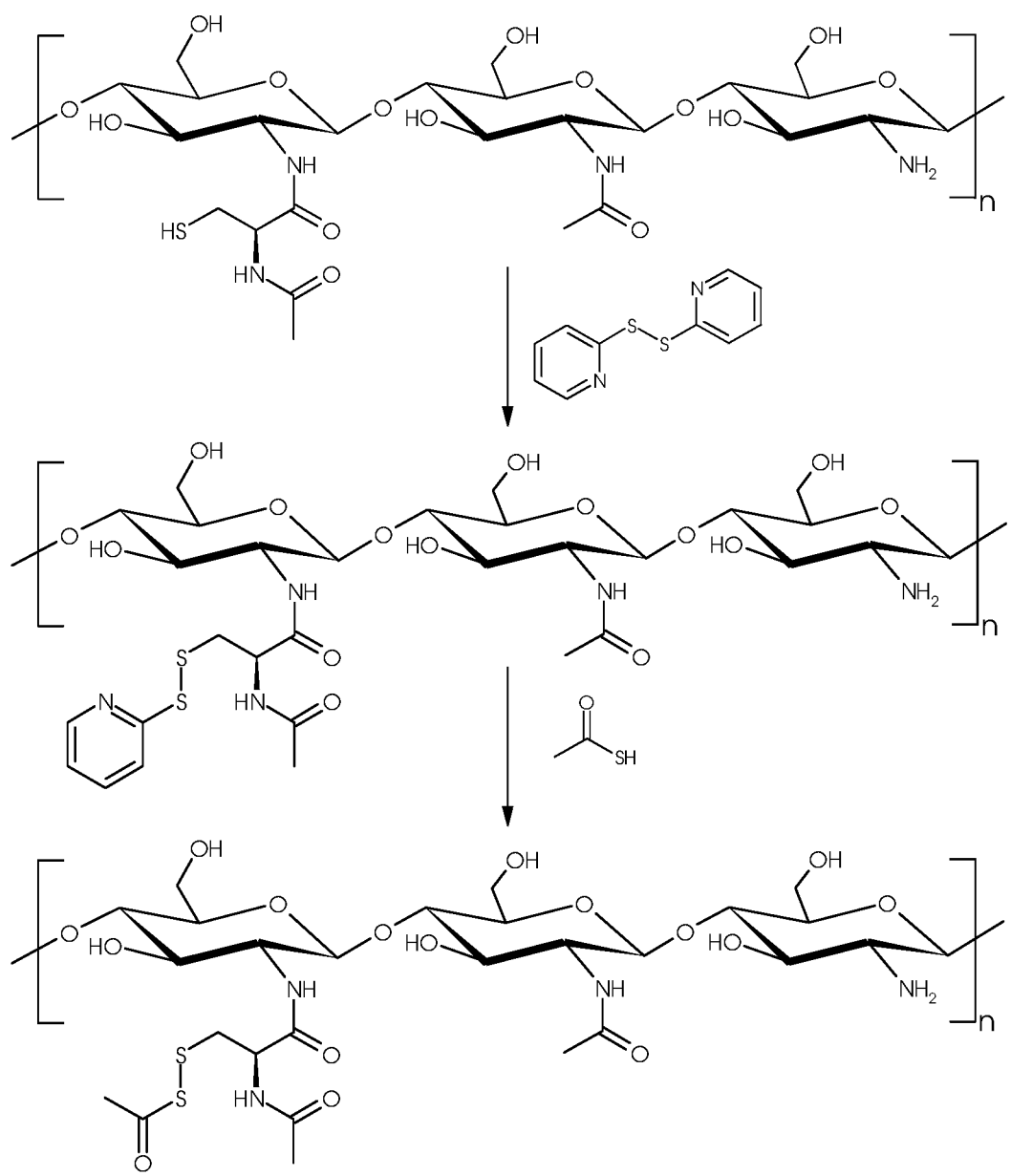

Chitosan-N-acetylcysteine hydrochloride (Chitosan-NAC), the starting material for a $H_2S$ releasing polymer according to FIG. 1C was synthesized according to a method described previously (WO 2015/169728 "Aqueous ophthalmic solution and method for treating dry eye syndrome"). Other routes for synthesis were published as well (Schmitz, Grabovac et al., 2008, Synthesis and characterization of a chitosan-N-acetyl cysteine conjugate, Int J Pharm (347): 79-85). The reaction scheme is depicted in FIG. 2.

2 g Chitosan-NAC (MW 150 kDa, degree of modification 185 g·mol thiol moieties/g polymer) were dissolved in 200 mL water (WFI, water for injection). About 90 mg (approx. 400 µmol) 2,2'-dithiodipyridine were dissolved in 5 mL ethanol and were admixed to the polymer solution. The solution was stirred for one hour at ambient temperature. Then, 76 mg (1 mmol) of thioacetic acid were dissolved in 0.5 mL 1 M NaOH and were added to the reaction solution. The solution was stirred for further 35 min. Thereafter, the solution was neutralized with NaOH and the polymer was precipitated by addition of 2-propanol. The polymer was harvested by suction filtration. For further purification, the polymer was suspended in WFI and strongly acidified (pH~1) with 5 M HCl. The polymer was again precipitated by addition of 2-propanol and harvested by suction filtration. The polymer was washed several times with 2-propanol and was finally dried under reduced pressure. 1.6 g polymer was obtained as a white, water-soluble powder with an estimated molecular weight of 150 kDa (based on the starting material) and a degree of modification with $H_2S$ releasing perthiol structures of 178 µM per g polymer. This corresponds to a conversion rate of 96% of the thiol moieties of the polymer used as starting material.

Example 2: Generation of an HS-Releasing Hyaluronic Acid Derivative

Figure 3:
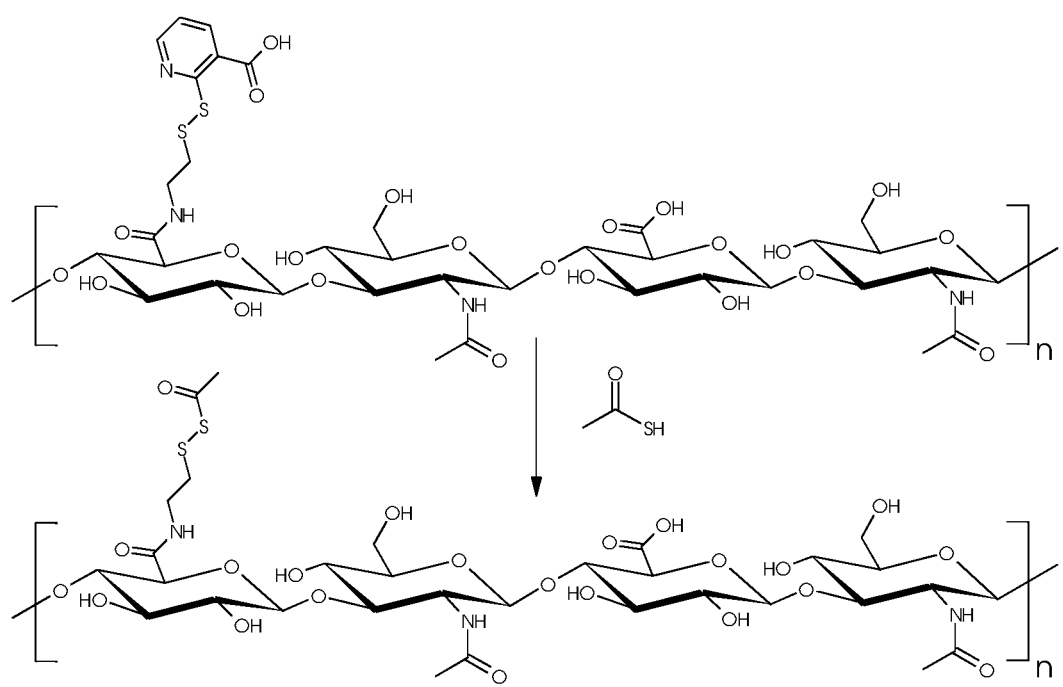

An S-mercaptonicotinic acid-protected thiolated hyaluronic acid derivative was used as intermediate for the introduction of acyl-protected perthiol groups to the polymer. The schematic reaction scheme of this synthesis step is shown in FIG. 3. The protection of thiol-groups of thiolated polymers via mercaptonicotinic acid (step b) and its derivatives is described in EP 2 482 852 "Mucoadhesive polymers having vitamin B partial structures".

Step a) Synthesis of 2-(2-aminoethyldisulfanyl)pyridine-3-carboxylic Acid

2-Mercaptonicotinic acid was dispersed in $H_2O$, and dissolved completely after addition of 5 M NaOH until pH was 9-10. After pH adjustment to about 8.0 with HCl, a 30% solution of $H_2O_2$ was added drop wise, while keeping the pH constantly in a range of 7.5-8.5. After acidification to pH=1.0-1.5 with 5 M HCl, the dimer compound 2-(3-carboxypyridin-1-ium-2-yl)disulfanylpyridin-1-ium-3-carboxylic acid precipitated as a white solid. The product was filtered and washed with 1 M HCl and 2-propanol. Finally, it was dried under reduced pressure at 50° C.

The dimer (2-[3-carboxypyridin-1-ium-2-yl]disulfanylpyridin-1-ium-3-carboxylic acid) was suspended in 96% ethanol and dissolved upon addition of triethylamine. A solution of cysteamine-HCl (1.1 equiv.) in 96% ethanol was neutralized with an equimolar amount of triethylamine. The cysteamine solution was added to the dimer solution and the mixture was allowed to react for 45 hours. The precipitate was filtered off, washed with ethanol and dried under reduced pressure at 50° C. (mp [uncorrected]=184-186° C.).

Step b) Synthesis of S-Mercaptonicotinic Acid-Protected Thiolated Hyaluronic Acid 1) 3.2 g of free hyaluronic acid (mean molecular weight (MMW) approximately 0.6 MDa) were suspended in 300 mL DMSO.
2) 900 µL of triethylamine were added.
3) The suspension was stirred at ambient temperature until complete dissolution of the hyaluronic acid-triethylamine salt.
4) The "pH value" of the solution was adjusted to 2.55 to 2.75 by addition of HCl in a suitable organic solvent.
5) 470 mg of N,N'-carbonyldiimidazole in 10 mL DMSO were added, and the solution was stirred for 30 min at ambient temperature.
6) 600 mg of 2-(2-aminoethyldisulfanyl)pyridine-3-carboxylic acid (s. step a) were added, and the solution was stirred for 20 hrs.
7) The reaction solution was acidified with 5 M HCl.
8) The S-mercaptonicotinic acid-protected thiolated hyaluronic acid was precipitated by addition of 2-propanol and harvested by centrifugation.
9) The polymer was dissolved in 300 mL $H_2O$ and re-precipitated with 2-propanol.
10) The polymer was harvested by centrifugation and dried under reduced pressure.

2.6 g of a white, water soluble powder was obtained with a degree of modification of about 250 g·mol mercaptonicotinic acid bearing sidechains/g polymer.

Step c) Synthesis of $H_2S$-Releasing Hyaluronic Acid Derivative Starting from the Product of Step b)

1) The polymer obtained in step 10 during the synthesis of S-mercaptonicotinic acid-protected thiolated hyaluronic acid as described above was dissolved in 300 mL $H_2O$ and the pH was adjusted to 7.3.

2) 228 mg (3 mmol) thioacetic acid was mixed with 1.50 mL 1 M NaOH and added to the polymer solution.
3) The solution was stirred for 15 min.
4) The solution was strongly acidified by addition of HCl.
5) The final polymer was precipitated by addition of 500 mL 2-propanol and harvested by centrifugation.
6) The solid polymer was suspended in 2-propanol, filtrated by suction, washed three times with 50 mL 2-propanol and twice with 50 mL ethanol, until the filtrate was colourless.
7) The polymer was dried under reduced pressure at 35-40° C.

2.4 g of a white, water soluble powder was obtained with an estimated degree of modification of about 250 µmol S-acetyl moieties and with an estimated molecular weight of 0.6 MDa (based on the starting material). The absence of aromatic signals in $^1$H-NMR spectra showed complete conversion of S-mercaptonicotinic acid-protected thiolated hyaluronic acid to the desired product.

Figure 5:
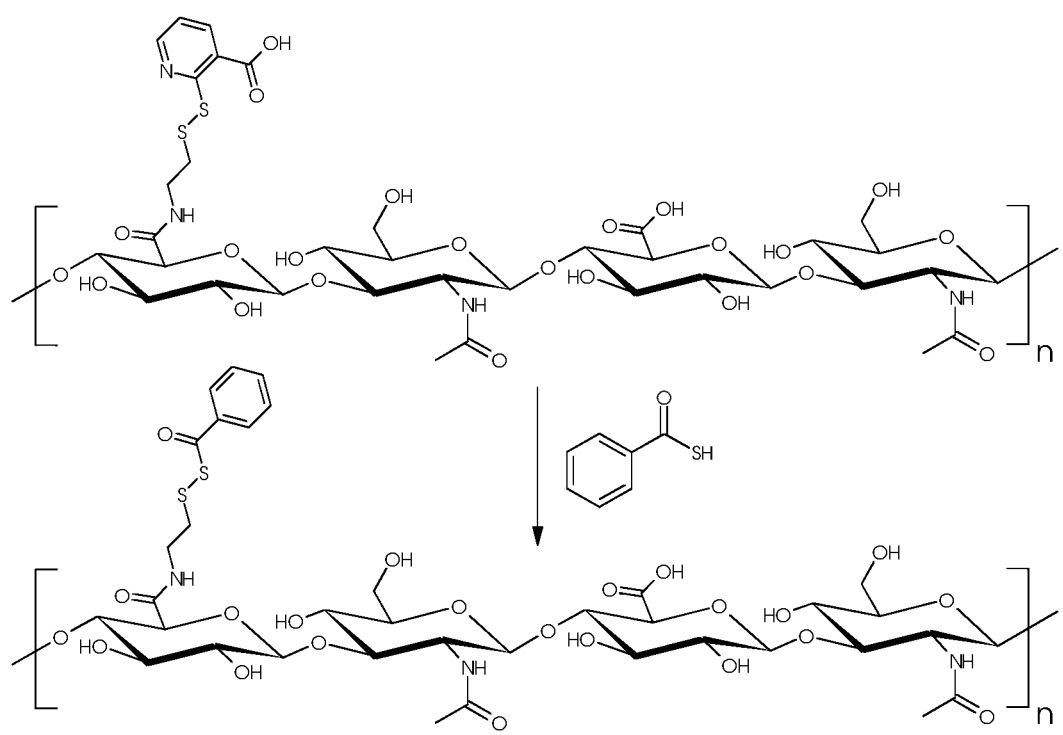

A similar synthesis was also applicable for generation of another $H_2S$-releasing hyaluronic acid derivative with thiobenzoic acid in step c) 2) as schematically shown in FIG. 5.

Figure 4:
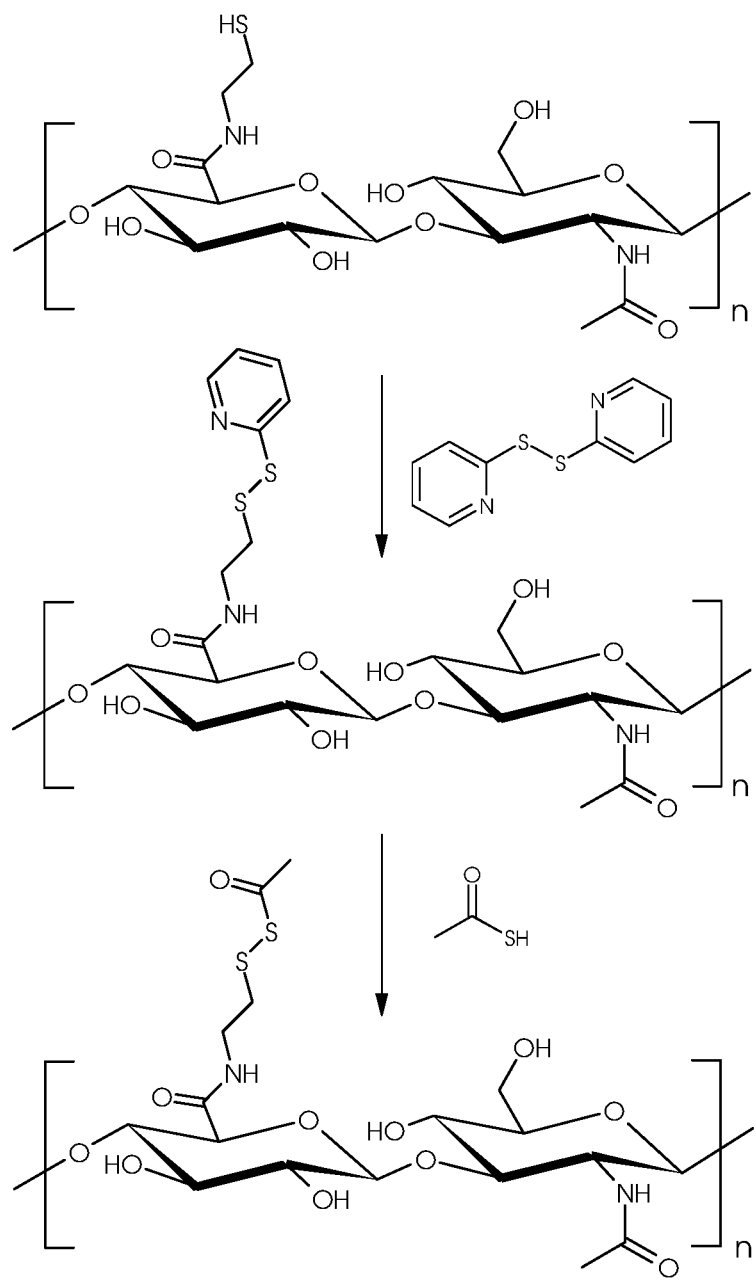

Example 3: Generation of an $H_2S$-Releasing Hyaluronic Acid Derivative-Alternative Synthesis Route Alternatively, $H_2S$ releasing hyaluronic acid derivatives were synthesized according to the reaction scheme depicted in FIG. 4 using a thiolated hyaluronic acid as starting material.

1 g of hyaluronic acid-cysteamine conjugate (degree of modification ~150 µmol thiol moieties per g polymer, MW 270 kDa) was dissolved in 100 mL WFI. About 45 mg (approx. 195 µmol) 2,2'-dithiodipyridine were dissolved in 1.5 mL ethanol and were admixed to the polymer solution. The solution was stirred for 2 hours at ambient temperature.

About 38 mg (approx. 490 µmol) thioacetic acid were dissolved in 245 µL 1 M NaOH and the resulting solution was added to the polymer solution. After two hours stirring at ambient temperature, the polymer solution was neutralized by the addition of NaOH. Upon addition of 2-propanol, the polymer precipitated. The product was harvested by suction filtration and purified by multiple washings with ethanol. Finally, the polymer was dried under reduced pressure.

850 mg polymer was obtained as a white, fibrous product with an estimated molecular weight of 270 kDa (based on the starting material) and a degree of modification with $H_2S$ releasing perthiol structures of 147 µM per g polymer. This corresponds to a conversion rate of 98% of the thiol moieties of the polymer used as starting material. The polymer was insoluble in water, but dissolved, after being suspended in WFI in presence of 10-fold excess L-cysteine, to a clear viscous solution while $H_2S$ was released. Emerging $H_2S$ was detected by embrowning Pb-acetate paper.

Example 4: Release of Hydrogen Sulfide

The investigated polymer compounds according to the invention (as shown in FIGS. 1A and 1C) were analyzed for their hydrogen sulfide release properties in presence of a thiol containing component with an amperometric detection device ($H_2S$ Micro-Sensor with $H_2S$ permeable membrane; AMT Analysenmesstechnik GmbH). The $H_2S$ release was triggered by the addition of L-cysteine.

Figure 6:
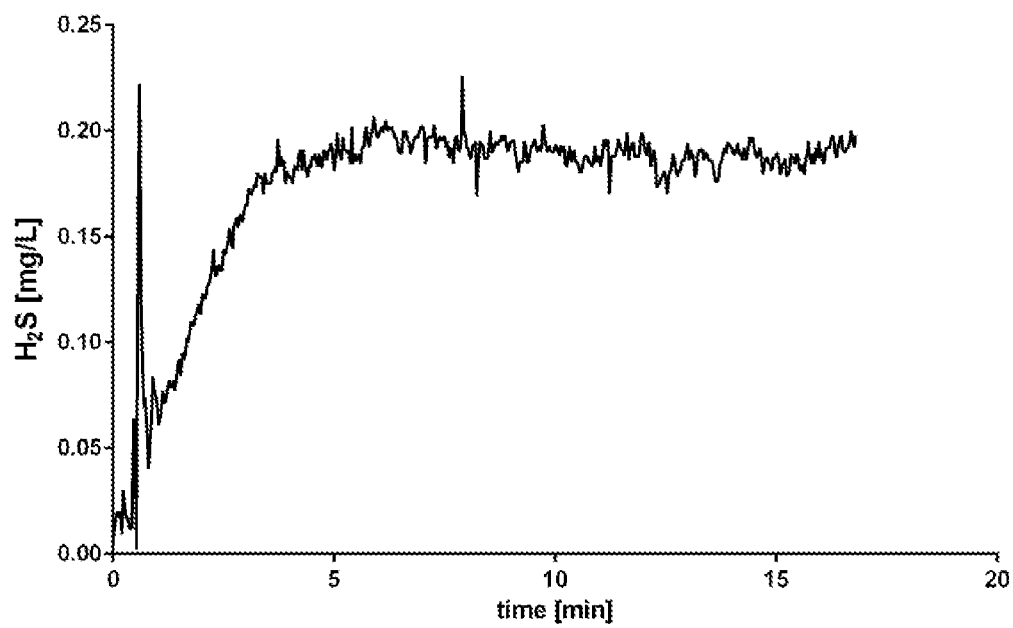
FIG. 6 shows the results from an $H_2S$ release assay, which was performed with an $H_2S$ releasing chitosan derivative.

FIG. 6 depicts the results of a $H_2S$ release assay, wherein 50 mL of a 0.1% (m/m) solution of the $H_2S$ releasing chitosan derivative, which was synthesized as described in example 1, was prepared with 50 mM acetate buffer (pH 5.5). To the resulting solution, which had a pH of 5.3, 1.5 mL of a 100 mM solution of L-cysteine were added. The resulting release of $H_2S$ was monitored at room temperature.

Figure 7:
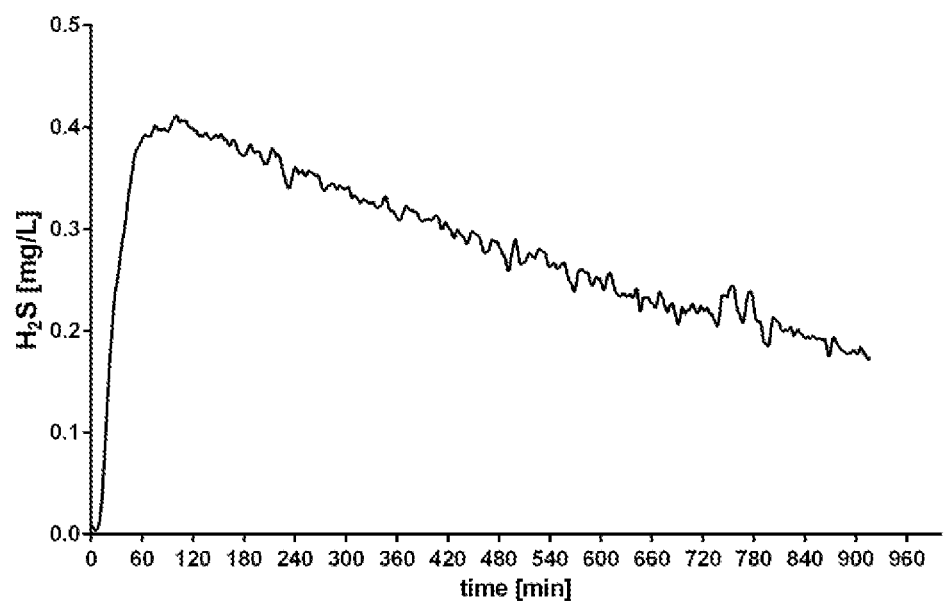
FIG. 7 shows the results from an $H_2S$ release assay, which was performed with an $H_2S$ releasing hyaluronic acid derivative.

FIG. 7 depicts the results of a $H_2S$ release assay, wherein 0.1% (m/m) of a $H_2S$ releasing hyaluronic acid derivative of example 2 (FIG. 1A) were incubated in DMEM (Dulbecco's modified eagle medium) in the presence of 3 mM L-cysteine (at room temperature and pH 7.6-7.8). After a short lag time, the $H_2S$ release continued for more than 15 hours at the investigated conditions.

Example 5: Cell Compatibility of $H_2S$-Releasing Polymer

In order to study cell compatibility, especially the effect of proliferation, the $H_2S$ releasing hyaluronic acid derivative according to FIG. 1A (s. above,) was investigated in comparison with unmodified HA (sodium salt of hyaluronic acid, "NA HA") and an S-mercaptonicotinic acid-protected thiolated hyaluronic acid ("Thiomer CAPPY"). As further control, the well established commercially available $H_2S$ donor N-(benzoylthio)benzamide (Donor 5a is NSHD1, a small molecule with a thiol activation mechanism) was included in the experiments.

Three types of skin cells were used as models: primary human dermal fibroblasts (dFb), the immortalized line of human microvascular endothelial cells (HMEC-1) and the keratinocyte cell line HaCat. The cells were cultured in their appropriate medium. Synthetic medium Fibrolife with supplements and gentamycin was used for dFb, EBM+ supplements was used for HMEC-1 and DMEM with 10% FCS and 1% CellShield was used for HaCat cells. Furthermore, 3 mM cysteine was added to all conditions investigated. The addition of 3 mM cysteine to all media did not affect cell growth as tested in pilot experiments. Cells were seeded and grown at least overnight before medium was changed and the HA components were added according to the agreed protocol. Two concentrations (0.05% and 0.1%) of HA samples were applied. The exposition was performed for 48 h and 96 h. During 48 h of experiment, one additional medium exchange was performed after 24 h of initial exposition. During 96 h of experiment, two additional medium exchanges were performed after 24 h and 72 h of initial exposition. Cell proliferation was measured indicated by using a WST-1-based colorimetric detection reagent according to manufacturers' protocol with fresh medium without addition of any HA-derivative. All experiments have been repeated 3-6 times each with 5 parallel samples of each condition. After each medium exchange the successful generation of $H_2S$ from was verified with Pb-acetate paper.

The study demonstrated that $H_2S$ releasing hyaluronic acid derivative is not toxic to the cell types analyzed here in the concentrations and culture settings used. The experimental outcome seems to be valid since known effects of induced fibroblast and endothelial cell proliferation by non-modified HA (0.1% conc.) could be observed. Endothelial cells might be most sensitive to $H_2S$ as found for "$H_2S$ CAPPY" and the control Donor 5a.

Example 6: Wound Healing Preparation—Sponge

An aqueous hydrogel solution comprising 1.5% (m/m) $H_2S$ releasing chitosan derivative with a degree of modification of about 185 µmol S-acetyl moieties according to the invention is prepared. The solution is cast into 12 well cell culture plates—in an amount of 0.9 g per well) and freeze dried. The resulting lyophilisate is a sponge with a round shape and has a diameter of about 2 cm. The sponges are sealed individually in pouches. The pouches and secondary packaging material are then sterilized via gamma irradiation.

For the treatment of wounds the sterile sponges are applied on the skin wound. A few drops of a sterile buffered solution of N-acetylcysteine in a concentration of 5 mg/mL may be applied on the sponge to immediately start the release of $H_2S$. The wound area is then covered with a secondary wound dressing with low gas permeability, such as a film consisting of polyethylene, polypropylene or polytetrafluoroethylene or a fabric or fleece that has reduced gas permeability, for example, a polypropylene fleece with an almost gas-tight layer such as polyurethane.

Example 7: Skin Treatment—Topical Hydrogel

An aqueous hydrogel solution comprising 1% (m/m) $H_2S$ releasing hyaluronic acid derivative with a degree of modification of about 250 g·mol S-acetyl moieties according to the invention is prepared in a phosphate buffer with a physiologically acceptable pH value. The solution is then filled into single use containers (e.g. single dose polypropylene containers or glass syringes with a filling volume of about 3 mL) and sterilized with moist heat. A second composition comprising N-acetylcysteine in a physiologic buffer solution in a concentration of 10 mg/mL is also provided in a single use container. The resulting hydrogel with a low viscosity is applied on intact skin or inflamed skin areas, immediately followed by the application of approximately the same amount of the composition comprising N-acetylcysteine to the same skin area.

The treatment with the hydrogel may be preferred in case of cosmetic skin conditions or skin disease such as for treatment of scars and closed wounds or inflammatory diseases of the skin.

Example 8: Wound Healing Preparation—Hydrogel

An aqueous hydrogel comprising 2% (m/m) $H_2S$ releasing hyaluronic acid derivative with a degree of modification of about 250 g·mol S-acetyl moieties according to the invention is prepared in a phosphate buffer with a physiologically acceptable pH. The gel is then filled into single use containers (such as syringes) and sterilized with moist heat.

The resulting hydrogel is applied on the skin wound. A small volume of a sterile buffered solution of N-acetylcysteine in a concentration of 100 mg/mL may be sprayed on the gel to immediately start the release of $H_2S$. The wound area is then covered with a secondary wound dressing with low gas permeability, such as a film consisting of polyethylene, polypropylene or polytetrafluoroethylene or a fabric or fleece that has reduced gas permeability, for example, a polypropylene fleece with an almost gas-tight layer such as polyurethane.

Example 9: Injectable Dermal Filler Formulation

Hyaluronic acid is stabilized via crosslinking with 1,4-butanediol diglycidyl ether (BDDE). After purification via dialysis the crosslinked hyaluronic acid is mixed with a buffered solution (phosphate buffer, pH 7.4 comprising a $H_2S$ releasing hyaluronic acid derivative according to the invention, so that the final concentration of $H_2S$ releasing hyaluronic acid derivative in the formulation is 5 mg/mL. The formulation is then filled into syringes and sterilized with moist heat.

The thiol-group containing reaction partner may be an endogenous reaction partner which is present in the skin, such as reduced glutathione.

Example 10: Wound Healing Preparation—Multi-Layer Wound Dressing

The $H_2S$ releasing polysaccharide polymer according to the invention may be provided in a multi-layer wound dressing (or dermal patch) as shown in FIG. 9. A reservoir of dry $H_2S$ releasing polymer powder 1 is used as the absorbent layer of the dressing. Optionally, this layer may additionally comprise a thiol-group donor such as L-cysteine, homocysteine, N-acetylcysteine or reduced glutathione. Alternatively, the thiol-group reaction partner is not applied but provided endogenously e.g. in the wound exudate. The absorbent layer is covered by an outer protective membrane with low gas permeability. The outer protective layer 2 further comprises a layer of adhesive, which is used to adhere the wound dressing to the skin. The outer layer 2 extends beyond the edges of the other layers (i.e., the absorbent layer 1 and the wound contact layer 4) to form an adhesive rim 4. The polymer reservoir is further covered by an inner non-adherent and porous membrane, for example, a woven nylon fabric. This wound contact layer 4 is permeable to fluids (wound exudate), hypoallergenic and non-irritant.

The wound contact layer 4 and the exposed part of the adhesive layer 2 are protected prior to use by a release-coated protective membrane. The protective membrane is formed from paper release-coated with a silicone.

The multilayered wound dressing is packaged in a hermetically sealed pouch and sterilised by gamma-irradiation.

Example 11: Injectable Formulation for the Treatment of Acne Scars

An aqueous hydrogel comprising 2% (m/m) $H_2S$ releasing hyaluronic acid derivative according to the invention with a degree of modification of about 250 µmol S-acetyl moieties is prepared in a phosphate buffer with a physiologically acceptable pH. A second composition comprising N-acetylcysteine in a physiologically acceptable buffer solution in a concentration of 0.5% (m/m) is prepared. The gel and the N-acetylcysteine solution are then filled into single use dual chamber syringes and sterilized with moist heat.

Example 12: Injectable Formulation for Intraarticular Viscosupplementation

An aqueous hydrogel comprising 1.0% (m/m) $H_2S$ releasing hyaluronic acid derivative according to the invention is prepared in a phosphate buffer with a physiologically acceptable osmolarity and pH value. The gel is filled into syringes and sterilized with moist heat.

The thiol-group containing reaction partner may be an endogenous reaction partner which is present in the synovial fluid, such as reduced glutathione.

Example 13: Injectable Dermal Filler

A hyaluronic acid-cysteamine derivative is stabilized via crosslinking with disulfide bonds (formation of cystamine bridges). The crosslinked hyaluronic acid is then mixed with a buffered solution (phosphate buffer, pH 7.4) comprising a $H_2S$ releasing hyaluronic acid derivative according to the invention, so that the final concentration of $H_2S$ releasing hyaluronic acid derivative in the formulation is 5 mg/mL. The formulation is then filled into syringes and sterilized with moist heat.

The thiol-group containing reaction partner may be an endogenous reaction partner, which is present in the skin, such as reduced glutathione.

Example 14: Injectable Dermal Filler

An aqueous hydrogel comprising 2.5% (m/m) $H_2S$ releasing hyaluronic acid derivative according to the invention is prepared in a phosphate buffer with a physiologically acceptable osmolarity and pH value. The gel is filled into syringes and sterilized with moist heat.

The thiol-group containing reaction partner may be an endogenous reaction partner which is present in the skin, such as reduced glutathione.

Example 15: Injectable Formulation for Intraarticular Viscosupplementation

An aqueous hydrogel comprising 0.5% (m/m) hyaluronic acid-cysteamine derivative and another aqueous hydrogel comprising 0.5% (m/m) $H_2S$ releasing hyaluronic acid derivative according to the invention are prepared in a phosphate buffer with a physiologically acceptable osmolarity and pH value. The gels are individually filled into dual chamber syringes and sterilized with moist heat.

Example 16: Eye Drop Formulation

An aqueous ophthalmic solution comprising 0.1% (m/m) $H_2S$ releasing chitosan derivative according to the invention is prepared in a borate buffer with a physiologically acceptable osmolarity and pH value. The solution is sterilized via filtration and filled into single use ophthalmic dosage units.

The thiol-group containing reaction partner may be an endogenous reaction partner, which is present on the ocular surface such as reduced glutathione.

Example 17: Intraocular Implant

An aqueous hydrogel comprising 4.0% (m/m) $H_2S$ releasing hyaluronic acid derivative according to the invention is prepared in a phosphate buffer with a physiologically acceptable osmolarity and pH value. The gel is filled into syringes and sterilized with moist heat.

The thiol-group containing reaction partner may be an endogenous reaction partner, such as reduced glutathione.

Example 18: Vitreous Body Substitute

A hyaluronic acid-cysteamine derivative is stabilized via crosslinking with disulfide bonds (formation of cystamine bridges). The crosslinked hyaluronic acid is then mixed with a buffered solution (phosphate buffer, pH 7.4) comprising a $H_2S$ releasing hyaluronic acid derivative according to the invention, so that the final concentration of $H_2S$ releasing hyaluronic acid derivative in the formulation is 3 mg/mL. The formulation is then filled into syringes and sterilized with moist heat.

The thiol-group containing reaction partner may be an endogenous reaction partner, such as reduced glutathione.

Example 19: Solid Intraocular Implant

Tablets with a weight of approximately 2 mg comprising 1 mg of a $H_2S$ releasing hyaluronic derivative with a degree of modification of about 250 μmol S-acetyl moieties according to the invention and 0.2 mg N-acetylcysteine are prepared. The tablets are sealed individually in pouches. The pouches and secondary packaging material are then sterilized via gamma irradiation.

Example 20: Preparation of 4-Amino-N-(Benzoylthio)Benzamide

4-Amino-N-(benzoylthio)benzamide is a $NH_2$-modified derivative of the $H_2S$ Donor 5a comprising a benzoylthiobenzamide substructure. The schematic reaction scheme of this synthesis is shown in FIG. 10A.

Step 1 Synthesis of S-benzoylthiohydroxylamine

To a stirred solution of 5.6 g KOH (100 mmol) in 150 ml $H_2O$ and 5.65 g (50 mmol) Hydroxylamine-O-sulfonic acid 7.25 g Thiobenzoic acid (52.5 mmol) were added. After stirring at ambient temperature for 1 hour, the precipitate was collected by suction filtration and dried under reduced pressure.

Step 2 Synthesis of N-(benzoylthio)-4-nitrobenzamide 7.12 g (46 mmol) of the crude S-benzoylthiohydroxylamine were dissolved in 250 ml $CH_2Cl_2$ and 3.6 g (46 mmol) of pyridine were added. 8.53 g (46 mmol) p-$NO_2$-benzoylchloride were suspended in 300 ml $CH_2Cl_2$ and added dropwise via dropping funnel. The reaction progress was monitored by TLC (hexane/diethylether=1:1.5), after 2 hours the solution was filtrated over a pad of Celite® and volatiles were removed under reduced pressure. The crude product was purified via silica gel column chromatography using hexane/diethylether=1:1.5 to give 3.52 g of a white solid (23% over 2 steps).

Step 3 Synthesis of 4-amino-N-(benzoylthio)benzamide 1.7 g (5.6 mmol) N-(benzoylthio)-4-nitrobenzamide were dissolved in a mixture of 270 ml THF and 180 ml $H_2O$ and cooled to 0° C. 2.42 g (14.07 mmol) of $Na_2S_2O_4$ were added, whereupon the solution turned yellow. The conversion was monitored via TLC (diethylether, $R_{f\ product}$~0.6). After 30 minutes, THF was removed quantitatively under reduced pressure and the aqueous solution was extracted with ethyl acetate. The organic layer was dried over $Na_2SO_4$ and volatiles were evaporated under reduced pressure to give 640 mg of a yellowish powder (45%). $^1H$ NMR (400 MHz, DMSO-d6) δ 9.52 (s, 1H, NH), 7.91 (d, J=7.3 Hz, 2H), 7.77-7.68 (m, 3H), 7.61 (d, J=7.7 Hz, 2H), 6.59 (d, J=8.6 Hz, 2H), 5.85 (s, 2H, $NH_2$)

Corresponding hydroxylated, phosphorylated or sulfonated derivatives can be prepared in analogy to the described protocol using various protecting group strategies.

A first olfactory test performed with 4-amino-N-(benzoylthio)benzamide dissolved in acetone/phosphate buffer indicated $H_2S$ liberation after addition of an excess amount of L-cysteine. This finding was later confirmed by detecting H₂S release after addition of excess amounts of L-cysteine or cysteamine to 4-amino-N-(benzoylthio)benzamide via embrowning Pb-acetate paper.

Example 21: Synthesis of a H₂S Releasing Hyaluronic Acid Derivative

Coupling of 4-amino-N-(benzoylthio)benzamide to hyaluronic acid is performed by dissolving hyaluronic acid in DMSO and triethylamine and adding a reagent which mediates amide coupling such as carbonyldiimidazole (CDI), carbodiimides such as dicyclohexylcarbodiimide (DCC), diisopropylcarbodiimide (DIC), phosphonium or aminium/uronium-umonium type reagents such as bromo-tripyrrolidino-phosphonium hexafluorophosphate (Py-BrOP®) or 2-(1H-benzotriazol-1-yl)-N,N,N',N'-tetramethylammonium tetrafluoroborate/hexafluorophosphate (TBTU, HBTU). After precipitation, the H₂S releasing hyaluronic acid derivative is isolated via filtration, washed and dried under vacuum.

Coupling of hydroxylated, sulfonated or phosphorylated 4-amino-N-(benzoylthio)benzamide derivatives to hyaluronic acid is performed under aqueous conditions by dissolving sodium hyaluronate in a phosphate buffer and adding a reagent which mediates amide coupling such as a water soluble carbodiimide (e.g. N-ethyl-N'-(3-dimethylaminopropyl)carbodiimide HCl, EDC.HCl) or a triazine derivative (e.g. 4-(4,6-dimethoxy-1,3,5-triazin-2-yl)-4-methylmorpholinium chloride, DMT-MM). After precipitation the H₂S releasing hyaluronic acid derivative is isolated via filtration, washed and dried under vacuum.

A schematic structure of the resulting H₂S releasing hyaluronic acid derivative is shown in FIG. 10B.

The invention claimed is:

1. A hydrogen sulfide releasing polymer compound comprising a polysaccharide backbone and at least two substructures,
    wherein said polysaccharide backbone is selected from the group consisting of hyaluronic acid, cellulose derivatives, salts of alginic acid, chondroitin sulfate, dermatan sulfate, chitosan, chitosan derivatives, pectin, and salts of pectin,
    wherein said substructures are capable of releasing hydrogen sulfide by thiol activation, and wherein each of the at least two substructures capable of releasing hydrogen sulfide by thiol activation:
        is covalently bound to the polysaccharide backbone, and
        is independently selected from the group consisting of acyl-protected perthiols, N-(acylthio)-benzamides, dithioperoxyanhydrides, arylthioamides, and diallyl disulfide or diallyl trisulfide structures derived from garlic.

2. The hydrogen sulfide releasing polymer compound according to claim 1, wherein the at least two substructures are acyl-protected perthiol substructures according to formula I

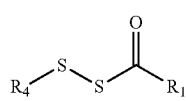

wherein $R_1$ is an alkyl, an alkenyl, an alkinyl, an alkylaryl, an aralkyl or an aryl group, and $R^4$ is an atom of a repetitive unit of the polysaccharide backbone to which the acyl-protected perthiol substructure is covalently bound.

3. The hydrogen sulfide releasing polymer compound according to claim 1, wherein the polymer compound comprises at least two substructures according to formula II

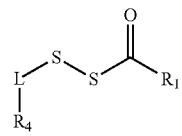

wherein $R_1$ is an alkyl, an alkenyl, an alkinyl, an alkylaryl, an aralkyl or an aryl, wherein $R_4$ is an atom of a repetitive unit of the polysaccharide backbone to which the substructure is covalently bound, and
wherein L is a linker.

4. The hydrogen sulfide releasing polymer compound according to claim 3, wherein the at least two substructures are selected from the group consisting of formula III

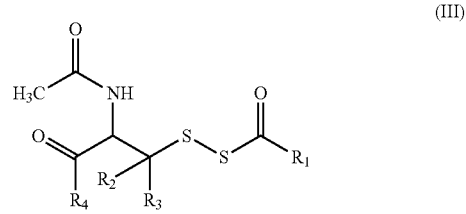

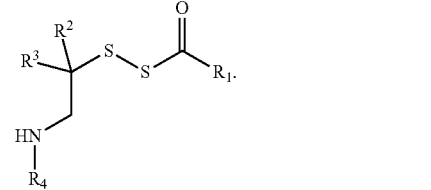

5. The hydrogen sulfide releasing polymer compound according to claim 1, wherein the polysaccharide backbone is chitosan or hyaluronic acid and the polysaccharide backbone has a mean molecular weight
    in the range of about 20 kDa to about 500 kDa if the polysaccharide backbone is chitosan or
    in the range of about 90 kDa to about 3 MDa if the polysaccharide backbone is hyaluronic acid.

6. The hydrogen sulfide releasing polymer compound according to claim 1, wherein the polysaccharide backbone is selected from hyaluronic acid and chitosan.

7. The hydrogen sulfide releasing polymer compound according to claim 2, wherein $R_1$ is selected from phenyl and methyl.

8. The hydrogen sulfide releasing polymer compound according to claim 3, wherein $R_1$ is selected from phenyl and methyl.

9. The hydrogen sulfide releasing polymer compound according to claim 1, wherein said substructures release essentially no hydrogen sulfide by hydrolysis.

10. The hydrogen sulfide releasing polymer compound according to claim 1, wherein each of the at least two substructures capable of releasing hydrogen sulfide by thiol activation is capable of releasing hydrogen sulfide upon contact with a thiol group bearing reaction partner, and wherein the thiol group containing reaction partner is selected from the group consisting of cysteine, cysteamine, N-acylcysteine, homocysteine, and glutathione.

11. The hydrogen sulfide releasing polymer compound according to claim 1, wherein said at least two substructures are the same.

12. The hydrogen sulfide releasing polymer compound according to claim 1, wherein the polysaccharide backbone is a sodium or calcium salt of alginic acid.

* * * * *